(12) United States Patent
Mazzio et al.

(10) Patent No.: US 8,367,121 B2
(45) Date of Patent: Feb. 5, 2013

(54) NUTRACEUTICAL AGENT FOR ATTENUATING THE NEURODEGENERATIVE PROCESS ASSOCIATED WITH PARKINSON'S DISEASE

(75) Inventors: Elizabeth Anne Mazzio, Tallahassee, FL (US); Karam F Soliman, Tallahassee, FL (US)

(73) Assignee: Florida A & M University, Tallahassee, FL (US)

( * ) Notice: Subject to any disclaimer, the term of this patent is extended or adjusted under 35 U.S.C. 154(b) by 97 days.

(21) Appl. No.: 12/658,307

(22) Filed: Feb. 6, 2010

(65) Prior Publication Data

US 2010/0150895 A1 Jun. 17, 2010

Related U.S. Application Data

(63) Continuation-in-part of application No. 12/220,810, filed on Jul. 29, 2008, now abandoned, which is a continuation-in-part of application No. 11/438,746, filed on May 22, 2006, now abandoned.

(60) Provisional application No. 60/739,980, filed on Nov. 23, 2005.

(51) Int. Cl.
*A61K 36/45* (2006.01)
*A61K 36/53* (2006.01)
*A61K 36/73* (2006.01)

(52) U.S. Cl. ........ 424/641; 424/732; 424/736; 424/730; 424/757; 424/765; 514/505; 562/562

(58) Field of Classification Search .................. None
See application file for complete search history.

(56) References Cited

U.S. PATENT DOCUMENTS 6,733,797 B1 * 5/2004 Summers ...................... 424/728
6,923,960 B2 * 8/2005 De Simone .................. 424/94.1
6,964,969 B2 * 11/2005 McCleary ..................... 514/283

FOREIGN PATENT DOCUMENTS

WO   WO 98/32464   * 7/1998
WO   WO 01/03696   * 7/2000

* cited by examiner

*Primary Examiner* — Susan Hoffman

(57) ABSTRACT

This invention describes a comprehensive nutraceutical designed to antagonize major mitigating factors to the degenerative process associated with Parkinson's disease. The formulation is comprised of a primary base of pyruvate, succinate, α-Ketoglutarate and/or oxaloacetate, niacin/NADH, fruit extracts, anthocyanins, further combined with specific macro/micronutrients, trace elements, amino acids, flavonoids and concentrated plant sources. The nutraceutical contains all natural substances that should mitigate many of the neurodegenerative processes known to be associated with PD. Mechanisms addressed are to prevent the loss of ATP/by 1-methyl-4-phenylpyridinium rotenone, scavenge hydrogen peroxide/$O_2.^-$, augment antioxidant enzymes, prevent dopamine (DA) oxidation to DA-quinone via inhibition of COX, $PLA_2$, LOX, xanthine oxidase, tyrosinase, prevent hyperhomocysteinemia, antagonize PARP-1 apoptosis, increase blood flow, glucose and oxygen delivery to the brain, potentiate mitochondrial function, antagonize glia iNOS and MAO or its products, chelate redox-active iron, inhibit heme oxygenase-1, inhibit alpha-synuclein aggregation, augment ATP storage, mediate anti-inflammatory effects via inhibition of PDE, MAPK p38/c-Jun NH2-terminal kinase/PGE2, antagonize excitotoxicity and downregulate N-methyltransferase, all of which contribute toward PD pathology.

4 Claims, No Drawings

NUTRACEUTICAL AGENT FOR ATTENUATING THE NEURODEGENERATIVE PROCESS ASSOCIATED WITH PARKINSON'S DISEASE

CROSS-REFERENCE TO RELATED APPLICATIONS

This application is a continuation in part of Ser. No. 12/220,810 filed Jul. 29, 2008, now abandoned, which is a continuation in part of Ser. No. 11/438,746 filed May 22, 2006 now abandoned, which claims the benefit under 35 USC 119 (e), of previous application No. 60/739,980 filed on Nov. 23, 2005, which are all herein incorporated by reference.

STATEMENT REGARDING FEDERALLY SPONSORED RESEARCH AND DEVELOPMENT

The U.S. government has certain rights to this invention as federal support was provided for by NIH Grant NCRR 03020.

TECHNICAL FIELD

This invention describes a nutritional composition and method of use for prevention of Parkinson's disease, therefore relating to the fields of nutrition, pharmacology, neurology, pathophysiology, medicine and movement disorders.

DESCRIPTION OF THE RELATED ART

Parkinson's disease (PD) is a complex neurodegenerative disorder involving the predominant loss of dopaminergic neurons in the substantia nigra pars compacta (SNc), subsequent decay of the nigrostriatal tract and associated movement anomalies such as rigidity, bradykinesia and tremor. The foremost pathological features associated with SNc degeneration (Burch and Sheerin, Lancet. 2005 Feb. 12-18; 365 (9459):622-7; Zhu X et al., Am J Alzheimers Dis Other Demen. 2004 November-December; 19(6):345-52) are mitochondrial abnormalities, ergogenic failure (Lestienne et al., J Neurochem. 1990 November; 55(5):1810-2, Schapira et al., J Neurochem. 1990 December; 55(6):2142-5), excessive dopamine (DA) oxidation, Lewy body deposition, a-synuclein/ubiquinated protein aggregation, heightened concentration of redox-active free iron and a gradual loss of neuromelanin (Gotz et al., J Neural Transm Suppl. 1990; 29:241-9; Nagatsu, J Neural Transm. 2002 May; 109(5-6):731-45; Tofaris and Spillantini, Mov Disord. 2005 August; 20 Suppl 12:S37-44) in and around the SNc. Further, the extensive loss of endogenous antioxidant enzyme systems and reduced glutathione (GSH) (Bharath et al., Biochem Pharmacol. 2002 September; 64(5-6):1037-48) can render even higher levels of oxidative stress and associated lipid/protein nitration (via ONOO—)/oxidation (via $O_2$, $H_2O_2$ and $OH^-$) (Johnson M D et al., Am J Pharmacogenomics. 2005; 5(4):259-70). These events are clearly evidenced by the accumulation of 3-nitrotyrosine, protein carbonyls, 8-hydroxyguanosine, malondialdehyde and hydroxynonenal in the SNc area (Hald and Lotharius. Exp Neurol. 2005 June; 193(2):279-90; Sato et al., Neurology, 2005 Mar. 22; 64(6):1081-3; Sato et al., Neurology. 2005 Mar. 22; 64(6):1081-3; Pennathur et al., J Biol Chem. 1999 Dec. 3; 274(49):34621-8). In addition, subsequent chronic inflammation (Takeuchi H et al., J Biol Chem. 2005 Mar. 18; 280(11):10444-54) further aggravates the problem involving microglial activation, astrogliosis, release of cytotoxic molecules, free radicals and glutamate all which can further conspire excitotoxic, apoptotic and necrotic neurodegenerative cell death. Susceptibility of these events to occur in the SNc of any one particular individual could be dependent upon a number of factors including: hereditary genetic mutations (ie parkin, DJ-1, PINK-I, LRRK2, park-1, ubiquitin-carboxy-terminal-hydrolase L1 (Fahn and Sulzer, NeuroRx. 2004 January; 1(1):139-54; Bertram and Tanzi, J Clin Invest. 2005 June; 115(6):1449-57; Hyun D et al., J Neurosci Res. 2005 Oct. 15; 82(2):232-44; Farrer et al., Neurology. 2005 Sep. 13; 65(5):738-40), defects in mitochondrial function (Finsterer et al., Neuroradiology. 2001 November; 43(11):997-1000; Arvanitakis et al., Neurology. 2004 Sep. 28; 63(6):996-1001; Klein et al., Mov Disord. 2005 August; 20(8):1021-30), exposure to environmental mitochondrial toxins, head trauma, viral/bacterial infections, metals, antipsychotic/antidepressant drugs (Semchuk et al., Neurology. 1992 July; 42(7):1328-35; Nguyen et al., Therapie. 2004 January-February; 59(1):105-12; Factor and Weiner, Mov Disord. 1991; 6(3):225-9) or rural/farm living (Allam et al., Neurol Res. 2005 March; 27(2):206-8; Logroscino, Environ Health Perspect. 2005 September; 113(9):1234-8).

To date, the standard medical treatment for PD involves the use of therapeutics that mitigate neurological effects through modulation/regulation of neurotransmitter function (ie. levodopa/dopa-decarboxylase inhibitors Sinemet® and Madopar®, dopamine agonists, catechol-o-methyltransferase inhibitors, monoamine oxidase (MAO) inhibitors, anti-cholinergics and surgical treatments) (Pal and Netravathi, J Indian Med Assoc. 2005 March; 103(3):168-70, 172, 174-6). The objective of this invention to provide a nutraceutical formulation/vitamin that PD patients can take orally, that will slow/halt the neurodegenerative process. And, the premise for the invention is based on experimental findings of protective agents in a number of experimental models that pertain specifically to PD.

The formulation is comprised of commercially available over the counter substances that independently or in combination block biological pathological events integral to SNc degenerative processes. In total, the detailed description of this document provides 1) a rationale for composition and utility 2) in-depth analysis of each deleterious mechanism(s) involved with PD pathology as relevant to the subject matter 3) a list of corresponding naturally derived substances that antagonize the described biochemical events and 4) optional natural plant extracts or food sources most concentrated in the desired chemical substances (TABLE 1) as determined from the United States Department of Agriculture (USDA)—Phytochemical Databases, Dr. Duke's Phytochemical and Ethnobotanical Database, Phytotherapies.org, Justesen J Chromatogr A. 2000 Dec. 15; 902(2):369-79, Hoffmann D. Herbal Material Medica and the center for New Crops & Plant Products (NewCROP) at Purdue University. In total, the nutraceutical agent is comprised of a pyruvate and/or oxaloacetate base, niacin with an optimal blend of specific macronutrients, micronutrients, amino acids, elements, flavonoids and plant derived compounds/extracts (See: TABLE 2).

More definitively, the constituents include nutraceuticals that are known to 1) spare the loss of ATP (adenosine triphosphate)/and neuronal cell death induced by PD model experimental toxins: 1-methyl-4-phenylpyridinium (MPP+) ±rotenone 2) augment neuronal mitochondrial respiratory function and oxidation of glucose via kinetic potentiation of complex I and IV activities 3) antagonize astrocyte/microglial cytokine/endotoxin inducible nitric oxide synthase (iNOS) and/or monoamine oxidase (MAO) 4) non-enzymatically scavenge hydrogen peroxide ($H_2O_2$) and/or superoxide ($O_2.^-$) 5) prevent the autoxidation of dopamine (DA) 6) block cell death induced by reactive oxygen species (ROS) or 6-hydroxydopamine (6-OHDA) and 7) reduce/chelate complex redox-active iron. Moreover constituents also include nutraceutical agents that are reported to 8) inhibit aggregation of alpha-synuclein 9) antagonize 1-methyl 4-phenyl 1,2,3,6-tetrahydropyridine (MPTP)/MPP+ mediated nuclear poly (ADP-ribose) polymerase-1 (PARP-1) activation 10) reduce hyperhomocysteinemia 11) attenuate DA-quinone formation via inhibition of cyclooxygenase (COX), phospholipase A2 ($PLA_2$), xanthine oxidase (XO), peroxidase, lipoxygenase (LOX) and tyrosinase (polyphenol oxidase—PPO) 12) block formation of toxic catecholamine derived o-semiquinones from hydroquinones 13) mediate anti-inflammatory effects in astrocytes/microglia via inhibition of phosphodiesterase (PDE), mitogen stress activated kinases pathways p38 (p38MAPK), c-Jun NH2-terminal kinase (JNK) and heme oxygenase-1 (HO-1) 14) down regulate production of prostaglandin $E_2$ ($PGE_2$) 15) antagonize excitotoxicity and augment inhibitory neurotransmission 16) augment endogenous antioxidant systems [catalase, superoxide dismutase (SOD) and glutathione peroxidase (GSH-PX)] 17) inhibit N-methyltransferase (NMT) activity—an enzyme thought to play a contributing role in PD and 18) augment genetic expression of nerve growth factors. Each of the mechanisms and respective formula components are discussed in the detailed description section of this document.

A prior art review for novel approaches taken to antagonize the neurodegenerative process associated with PD include experimental/trial use of SOD/catalase/peroxidase mimetics (Peng et al., J Biol Chem. 2005 Aug. 12; 280(32):29194-8; U.S. Pat. No. 6,984,636 Murphy et al, Jan. 10, 2006; U.S. Pat. No. 6,573,257 Malfroy-Camine, et al. Jun. 3, 2003), antiapoptotic MAO inhibitors, independent or combination MAO inhibitor/metal chelators (Youdim et al., J Neurosci Res. 2005 Jan. 1-15; 79(1-2):172-9; Mandel et al., Brain Res Brain Res Rev. 2005 April; 48(2):379-87; Weinreb et al., Ann N Y Acad Sci. 2005 August; 1053:348-55; Zheng et al., J Neurochem. 2005 October; 95(1):68-78; WO-2004/006856, Andersen J, Jan. 22, 2004), cholinesterase/MAO inhibitors (Youdim et al., Mech Ageing Dev. 2005 February; 126(2):317-26), iron chelator/antioxidant/anti-inflammatory combinations (Mandel et al., Neurosignals. 2005; 14(1-2):46-60; Mandel et al., J Mol Neurosci. 2004; 24(3):401-16; U.S. Pat. No. 6,900,338, Haj-Yehia May 31, 2005), anti-inflammatory agents (Cleren et al., J Neurochem. 2005 August; 94(4):995-1004), histamine antagonists (U.S. Ser. No. 07/954,258 Kaminski, Sep. 30, 1992), NOS inhibitors, (Klivenyi et al., Neuroreport. 2000 Apr. 27; 11(6):1265-8; Watanabe et al., Eur Neuropsychopharmacol. 2004 March; 14(2):93-104), COX-2 inhibitors (WO2004/058163 Mark and Hathaway, Dec. 19, 2003; U.S. 60/373,317 Stephenson et al., Apr. 18, 2002), JNK inhibitors (U.S. Ser. No. 6,987,184 Sakata et al., Jan. 17, 2006; U.S. Pat. No. 6,949,544, Bethiel et al., Sep. 27, 2005; Wang et al., Neurosci Res. 2004 February; 48(2):195-202; Teismann et al., Proc Natl Acad Sci U S A. 2003 Apr. 29; 100(9):5473-8; Kuan and Burke, Curr Drug Targets CNS Neurol Disord. 2005 February; 4(1):63-7; Silva et al., Mov Disord. 2005 June; 20(6):653-64), phytic acid (U.S. Pat. No. 5,206,226, Sabin Apr. 27, 1993), vitamin E (Testa et al., Brain Res Mol Brain Res. 2005 Mar. 24; 134(1):109-18), vitamin C, coenzyme $Q_{10}$, lipoic acid (Virmani A et al., Ann N Y Acad Sci. 2005 August; 1053:183-91; Bhat and Weiner, Minerva Med. 2005 June; 96(3):145-54; Shults, Pharmacol Ther. 2005 July; 107(1):120-30; Etminan et al., Lancet Neurol. 2005 June; 4(6):362-5), creatine (Andres et al., Neuroscience. 2005; 133 (3):701-13; U.S. Ser. No. 09/283,267 Kaddurah-Daouk and Beal, Apr. 1, 1999), creatine/COX-2 inhibitors (Klivenyi et al., J Mol Neurosci. 2003; 21(3):191-8), ginsenoside Rg1 from ginseng (Chen et al., Acta Pharmacol Sin. 2005 January; 26(1):56-62), ginseng extract (Van Kampen et al., Exp Neurol. 2003 November; 184(1):521-9), N-acetyl-L-cysteine (NAC), thiol antioxidants (Bahat-Stroomza et al., Eur J Neurosci. 2005 February; 21(3):637-46), glutathione (U.S. Pat. No. 6,896,899 Demopolos et al., May 24, 2005) glycine, serine (CA 2454337 Heresco-Levy and Javitt, Aug. 6, 2004), ginko biloba extracts (SG-01126465, Tongxin Aug. 14, 2001; WO-2006/004386 Rojas Castaneda, Jul. 2, 2004), green tea extract/catechins (US2002151506 Castillo et al., Oct. 17, 2002), myelin associated protein antibodies (U.S. Pat. No. 5,684,133, Schwab et al. Nov. 4, 1997), nerve growth factors (Levy et al. BioDrugs, 2005; 19(2):97-127; Slevin et al., J Neurosurg. 2005 February; 102(2):216-22), phenoxyphenyl derivatives (U.S. Pat. No. 5,430,063, Ruigt et al. Jul. 4, 1995), melanin (U.S. Pat. No. 5,210,076 Berliner et al., May 11, 1993), hormones (U.S. Pat. No. 4,902,680, Aroonsakul Feb. 20, 1990), dehydroepiandrosterone (D'Astous et al., Synapse. 2003 January; 47(1):10-4), estrogen receptor agonists (D'Astous et al., Neuropharmacology. 2004 December; 47(8):1180-8), adenosine A2 receptor antagonists (Shiozaki et al., Psychopharmacology (Berl). 1999 November; 147(1): 90-5; Ikeda et al., J Neurochem. 2002 January; 80(2):262-70; Xu et al., Pharmacol Ther. 2005 March; 105(3):267-310; Pierri et al., Neuropharmacology. 2005 March; 48(4):517-24), AMPA antagonists (Abraham et al., Bioorg Med Chem. 2000 August; 8(8):2127-43), mGlu2/3 metabotropic and glutamate receptors agonists (Battaglia et al., Neuropharmacology. 2003 August; 45(2):155-66), acupuncture (Kim et al., Neurosci Lett. 2005 Aug. 12-19; 384(1-2):133-8), free radical spin traps (Matthews et al., Exp Neurol. 1999 May; 157 (1):120-6), transglutaminase inhibitors (ie. cystamine) (U.S. Ser. No. 60/444,563 Mouradian and Junn, Feb. 2, 2003) and angiotensin-converting enzyme inhibitors (Kurosaki et al., Eur Neuropsychopharmacol. 2005 January; 15(1):57-67).

Further, patent literature describing nutraceutical formulations that may apply to the treatment of PD or mitochondrial disorders include: 1) a nutraceutical comprised of tyrosine, iron and at least one selected from the group consisting of vitamin $B_6$, folate, vitamin $B_3$ or zinc to enable dopamine synthesis, secretion and transport for treatment of PD (WO-98/32464 Bridgeman and McMunn, Jan. 27, 1998) 2) a nutraceutical for improving memory, comprised of at least one phosphoester, at least one herbal antioxidant±amino acids, vitamins, where the primary component plays a critical role in neurotransmitter function within the hippocampus (U.S. Pat. No. 6,733,797, Summers May 11, 2004) 3) a nutracetuical formulation comprising acetyl L-carnitine, lipoic acid, coenzyme $Q_{10}$, Vitamin E and selenomethionine suitable for counteracting oxidative stress or mitochondrial pathologies (U.S. Ser. No. 09/968,986 De Simone, Oct. 3, 2001), 4) a formulation comprised of at least one essential fatty acid, at least one of vitamin $B_{12}$, folic acid and vitamin $B_6$, for treatment of any disease related to homocysteine (WO2001/003696, Horrobin and Gouaille, Jul. 11, 2000) and 5) a nutraceutical for treating degenerative disorders comprised of a) an agent that promotes ATP production selected from creatine, lipoic acid or trimethyl glycine b) at least one agent for scavenging free radicals selected from taurine, ginko, acetyl-L-carnitine, vinpocetin, lipoic acid, coenzyme Q10 and resveratrol c) at least one agent for maintaining membrane function selected from the group consisting of inositol and choline d) at least one agent for maintaining neurotransmitter function selected from DMAE or choline and e) at least one agent that downregulates cortisol, comprising pyridoxine and an agent that blocks apoptosis comprising huperzine (U.S. Pat. No. 6,964, 969, McCleary, Nov. 15, 2005).

The formulation that comprises this invention as set forth is specifically designed for PD and relates to blocking dopaminergic toxicity of the SNc and downstream deleterious events.

BRIEF SUMMARY OF INVENTION

The invention disclosed describes a nutraceutical agent comprised of one or more of glycolysis ergogenics 1) pyruvate, succinate, oxaloacetate±Vit. B3, Vit. B3 derivatives such as NADH, magnesium, acetyl-L-carnitine, alpha-ketoglutarate, phospho(enol)pyruvate, fructose and fructose 1,6 bisphosphate 2) two or more of fruit extracts, liquid concentrates or powders of raspberry, blueberry, bilberry, orange, lemon, strawberry, grape-seed extract, red grapes, cherry, elderberry, acai, apple, chokeberry, carrot, cranberry, apricot and pear and 3) at least two or more antioxidants selected from the group consisting of green tea extract, epigallocatechin gallate, seed coat of black soybean and anthocyanins wherein said anthocyanins further comprise aurantinidin, cyanidin, delphinidin, europinidin, luteolinidin, pelargonidin, malvidin, peonidin, petunidin and rosinidin and 3) antiapoptotic agents selected from resveratrol, naringin, shikonin, gromwell root, black cumin seed or tymoquinone and 4) optionally, lysine. The base is further combined in a blend with 5) water soluble/fat soluble vitamins, one or more of cytochrome C, magnesium, selenium, chromium, zinc, potassium, phosphorous, specifically defined amino acids, lipoic acid, evening primrose oil, canola oil, fish oil, sesame oil and/or concentrates/extracts of specific plants highest in these desired substances. These include aloe vera, barberry, calendula, celery seed, chamomile, cilantro, cacao beans, cinnamon, dill, echinacea, faba bean, fennel, garlic, ginko biloba, green tea, hyssop, licorice, marshmallow, meadowsweet, milk thistle, mulberries, oregano, parsley, peppermint, propolis, pumpkin seed, rosemary, sage, shark cartilage, skullcap, sorghum, soy, tumeric, basil, thyme and/or their isolated polyphenolic chemical constituents.

This invention aims to define a multi-factorial blend that augments anaerobic glycolysis, attenuates the loss of ATP and toxicity brought about by PD model toxins: 1-methyl-4-phenylpyridinium/rotenone, prevents the autoxidation of dopamine (DA) and/or attenuates enzymatic DA-quinone formation via inhibition of COX, $PLA_2$, LOX, xanthine oxidase, tyrosinase, blocks the formation of toxic DA o-semiquinones, prevents hyperhomocysteinemia, antagonizes PARP-1 apoptosis, potentiates mitochondrial complex I and IV function/OXPHOS, antagonizes glia iNOS and MAO or its products, scavenge hydrogen peroxide/$O_2.^-$ and/or augment endogenous antioxidant enzymes, reduces/chelates redox-active iron and/or inhibits heme oxygenase-1, inhibits aggregation of alpha-synuclein, increases blood flow, glucose and oxygen delivery to the brain, augments ATP storage, mediates anti-inflammatory effects via inhibition of PDE, MAPK p38/c-Jun NH2-terminal kinase or PGE2, antagonizes excitotoxicity and downregulates N-methyltransferase all which contribute to the origination of endogenous mitochondrial poisons structurally similar to MPP+.

DETAILED DESCRIPTION OF THE PREFERRED EMBODIMENT

The detailed descriptive section discloses information on specific deleterious mechanism(s) involved with PD pathology relevant to each aspect of the formulation. These are further classified under three broad categories (Formula Components A)—Energy Failure (Formula Components B)—Catecholamine Oxidation and (Formula Components C)—Inflammation. The preferred constituents integral to the formulation as they are first discussed will be denoted by a * (high preference)  (moderate preference), * (low preference) and no indication (no preference or preference undetermined). The formulation is summarized by mechanism and constituent, and constituent by appropriate plant source (if applicable) in TABLE 1. The formulation as a composite in its preferred form is comprised of carboxylic acids, macronutrients, micronutrients, elements, amino acids, plant polyphenols/flavonoids and plant sources as in the example presented in TABLE 2.

A. FORMULA COMPONENT A—AGENTS THAT PREVENT MITOCHONDRIAL ENERGY MALFUNCTION±AUGMENT ATP PRODUCTION VIA ANAEROBIC GLYCOLYSIS. The first issue addressed with the formulation is mitochondrial impairment, which is instrumental in mitigating the degenerative loss of nigrostriatal function associated with PD. It is well known that a defect of SNc complex I function is evident in human PD patients, and mitochondrial toxins such as MPP+, rotenone or endogenous isoquinolines initiate a loss of SNc aerobic energy (ATP) production through inhibiting mitochondrial complex I and/or IV and precede a neuropathological sequel analogous to human PD (Kotake Y and Ohta S. Curr Med Chem. 2003 December; 10 (23):2507-16; Nagatsu Neurosci Res. 1997 October; 29(2):99-111; Mazzio and Soliman, Biochem Pharmacol. 2004 Mar. 15; 67(6):1167-84.). With that, the initial mitochondrial insult appears to be the preeminent event in triggering downstream neuronal cell loss in the SNc and locus coeruelus (LC), with lesser extent of damage to other areas of the brain. For this reason, the first nutraceutical component addresses ergogenic failure in the presence of PD model mitochondrial toxins and its direct biological downstream effect. It is believed that mitochondrial toxins such as MPP+ gain entrance into SNc DAergic neurons through the dopamine transporter (DAT) system (Miller et al., Trends Pharmacol Sci. 1999 October; 20(10):424-9; Del Zompo et al., Br J Pharmacol. 1993 June; 109(2):411-4) and initiate a predictable loss of ATP requiring systems (Nakamura and Vincent, Neurosci Lett. 1986 Apr. 24; 65(3):321-5), one of which is the regulation, storage and axonal transport of DA and its synaptic release at the nerve terminal (Tanaka et al., Brain Res. 1976 Oct. 15; 115(2):273-83; Kiuchi et al., Neurosci Lett. 1992 Dec. 7; 147(2):193-6). The loss of ATP driven vesicular monoamine transporter-2 (VMAT2) is thought to render impaired DA uptake into synaptic vesicles (where DA is stable due to low pH) resulting in its accumulation in the cytosolic compartment (where it becomes highly unstable, subject to massive oxidation and forms neurotoxic oxidative metabolites of DA). In addition, unsequestered catecholamine oxidative products can further perpetuate oxidative stress, and act as a mitochondrial toxin independently due to their inherent unique ability to reduce heme containing substances such as the cytochromes within complex II-IV (Mazzio et al., Brain Res. 2004 Apr. 9; 1004(1-2):29-44).

Cellular production of ATP is critical for neuronal packaging due to the energy requirements of the DA transporter VMAT2. VMAT2 is inherently classified under the toxin-extrusion antiporter gene family which sequesters and detoxifies potential biological poisons (Miller et al., Trends Pharmacol Sci. 1999 October; 20(10):424-9). A reduction of VMAT2 function/mRNA is clearly evident in SNc degenerating neurons, the process of aging and after MPTP administration in vivo (Kurosaki et al., Metab Brain Dis. 2003 June; 18(2):139-46; Jourdain et al., J Neuroendocrinol. 2005 August; 17(8):509-17; Hogan et al., J Neurochem. 2000 May;

74(5):2217-20; Harrington et al., Brain Res Mol Brain Res. 1996 February; 36(1):157-62; Frey et al., Ann Neurol. 1996 December; 40(6):873-84) or MPP+ in vitro (Reinhard et al., J Neurochem. 1990 July; 55(1):311-20; Staal and Sonsalla, J Pharmacol Exp Ther. 2000 May; 293(2):336-42). These findings clearly suggest ergogenic failure to proceed DA related toxicity. Mitochondrial toxins such as MPP+ can also contribute to the failure of DA vesicular uptake by 1) directly impairing the function of VMAT2 2) binding directly to VMAT2, gaining entrance into synaptic vesicles and initiating extrusion of DA back into the cytoplasmic compartment (Przedborski S et al., Parkinsonism Relat Disord. 2005 June; 11 Suppl 1:S3-7) or by 3) blocking DA binding to striatal vesicular transporters thereby preventing normal DA sequestration (Vaccari and Saba, Eur J Pharmacol. 1995 Mar. 16; 292(3-4):309-14). In either case, mitochondrial toxins such as MPP+ pre-empts rampant cytosolic accumulation of DA, its oxidation at a neutral pH, conversion to neurotoxic DA-quinones, o-semiquinones, dopaminergic poisons and related free radicals (Ren et al., J Biol Chem. 2005 Oct. 7; 280(40): 34105-12; Choi et al., Neurochem Int. 2005 March; 46(4): 329-35) massive DA release from nerve terminals and decay of the striatal tract (Chang and Ramirez, Brain Res. 1986 Mar. 12; 368(1):134-40). Further, animals that display heightened dopaminergic SNc VMAT2 capabilities demonstrate a species resistance to systemic injection of MPTP (Staal et al., J Pharmacol Exp Ther. 2000 May; 293(2):329-35) even with substantial SNc MPP+ uptake and loss of ATP (Sundstrom and Samuelsson Pharmacol Toxicol. 1997 November; 81(5): 226-31). In contrast, a loss of VMAT2 (ie. heterozygote genetic knockout animals, administration of VMAT2 inhibitors) tends to exacerbate MPTP toxicity and associated inflammatory response in rodents (German et al., Neuroscience. 2000; 101(4):1063-9; Gainetdinov et al., J Neurochem. 1998 May; 70(5):1973-8). These findings indicate that DA oxidation/VMAT2 failure is second to the loss of ATP, but of equal importance in instigating the neurodegenerative sequel and each of which is addressed in the following sections regarding formulate components.

The next significant event initiated by the loss of neuronal SNc ATP is a predicable depolarization of the neuronal plasma membrane which can preempt: 1) release of Mg+ as a voltage dependent N-methyl-D-aspartate (NMDA) block at presynaptic receptors (Henneberry et al., Prog Clin Biol Res. 1989; 317:143-56; Novelli et al., Brain Res. 1988 Jun. 7; 451(1-2):205-12) 2) greater susceptibility to excitatory postsynaptic inward $Ca^{+2}$ currents in response to glutamate activation on ionotropic NMDA/AMPA/kainate receptors 3) a loss of inhibitory GABA metabotropic-inward ion currents upon receptor activation (Mereu et al., J Neurosci. 1991 May; 11(5):1359-66; Guatteo et al., Neurotoxicology. 2005 October; 26(5):857-68) and 4) excitotoxic neurodegenerative injury (Beal, Ann Neurol. 1992 February; 31(2):119-30). These events can trigger massive accumulation of cytosolic $Ca^{+2}i$ with inefficient $Ca^{+2}$ efflux mechanisms, rendering vulnerability to excitotoxicity upon activation of SNc NMDA receptors (Nakashima et al., J Neurophysiol. 1996 February; 75(2):740-9). The rise in $Ca^{+2}i$ can then precede a range of destructive neurodegenerative events such as activation of $Ca^{+2}$ dependent proteases/endonucleases, phospholipases and constitutive nNOS/mtNOS which can then initiate protein nitration/aggregation (Przedborski S et al., Parkinsonism Relat Disord. 2005 June; 11 Suppl 1:S3-7) or form the lethal molecule peroxynitrite (ONOO—) upon reactivity of NO with superoxide ($O_2.^-$) (Schulz et al., Mol Cell Biochem. 1997 September; 174(1-2):193-7). The over-excitability of striatal neurons is apparent after administration of MPTP, loss of energy and preempts a rapid influx of $Ca^{+2}$/calpain activation in the cytosolic compartment (Chera et al., Ann N Y Acad Sci. 2002 June; 965:274-80) with a reversal of toxicological damage by administration of calpain inhibitors (Turski et al., Nature. 1991 Jan. 31; 349(6308):414-8; Greenamyre and O'Brien, Arch Neurol. 1991 September; 48(9):977-81; Higuchi et al., J Biol Chem. 2005 Apr. 15; 280(15):15229-37; Loschmann et al., J Neural Transm Suppl. 1994; 43:133-43; Kanthasamy et al., Brain Res. 1997 Jun. 6; 759(1):1-8).

The initial loss of ATP in the SNc area can trigger two major events being 1) catecholamine oxidation due to faulty DA sequestration and 2) excitotoxic cell death (Beal, Ann Neurol. 1998 September; 44(3 Suppl 1):S110-4; Sonsalla et al., Amino Acids. 1998; 14(1-3):69-74). While the later two events will be addressed in subsequent sections of this embodiment, the very first formula component (A) incorporates substances that prevent the initial loss of ATP in the presence of PD model mitochondrial toxins (ie. MPP+, rotenone). This can be accomplished by augmenting neuronal metabolic compensatory systems (ie. substrate level phosphorylation) that drive ATP production when mitochondria are compromised (Mazzio and Soliman, Neurotoxicology. 2003 January; 24(1):137-47).

The effects of MPP+ can be reversed by overcoming the deprivation of ATP that occurs after MPP+ mediated halt of respiratory function via complex I and/or IV (Mazzio and Soliman, Biochem Pharmacol. 2004 Mar. 15; 67(6):1167-84; Desai et al., Brain Res. 1996 Apr. 9; 715(1-2):1-8). While there are a number of downstream events that can occur due to a loss of ATP, such as mitochondrial transition pore opening, apoptosis (Nicotra and Parvez, Neurotoxicol Teratol. 2002 September-October; 24(5):599-605; Liou et al., FASEB J. 2005 August; 19(10):1350-2; Chu C T et al., J Neurochem. 2005 September; 94(6):1685-95; Bo et al., Neurosci Res. 2005 October; 53(2):183-8; (Przedborski S et al., Parkinsonism Relat Disord. 2005 June; 11 Suppl 1:S3-7) and microtubular/cell structure collapse (Cappelletti G et al., FEBS Lett. 2005 Aug. 29; 579(21):4781-6), the critical event is to prevent the initial loss of ATP. Previous findings have demonstrated that MPP+ does mitigate a loss of complex I and IV function, however the decline in ATP corresponds to diminishing glucose concentrations (ie mimicking hypoglycemia) that result from rapid glycolytic substrate level phosphorylation in an attempt to sustain ATP (Mazzio and Soliman, Brain Res. 2003 Feb. 7; 962(1-2):48-60). Therefore, simply providing additional glucose supply can completely protect against the toxic effects of MPP+ in vitro, without reversing the damage to the mitochondria.

While our studies indicate that propelling the capacity of anaerobic glycolysis can overcome MPP+ insult in vitro, there may be doubt as to correlation in vivo given the high oxidative metabolic activity of the brain. However, a number of studies suggest that glucose metabolism in the brain plays a critical role in PD pathology. For example, the administration of MPTP in vivo, pre-empts robust glucose utilization (detected with [$^{2-14}$C]deoxyglucose) predominantly in the SNc and LC, areas that are most affected by PD (Palacios and Wiederhold, Brain Res. 1984 May 28; 301(1):187-91). In primates, the administration of MPTP evokes rapid uptake of 2-deoxy-D-[$^{14}$C]glucose in SNc/globus pallidus areas parallel to degenerative injury (Palombo et al., Brain Res. 1988 Jun. 21; 453(1-2):227-34; Schwartzman and Alexander G M, Brain Res. 1985 Dec. 9; 358(1-2):137-43; Schwartzman et al., Exp Neurol. 1988 December; 102(3):307-13) and the effects of MPTP/MPP+ invoke a rise in striatal lactic acid to an extent that parallels DA release (Kindt et al., J Pharmacol Exp Ther. 1987 September; 242(3):858-63; Rollema et al., Toxicology. 1988 May; 49(2-3):503-11), effects which an be blocked by DA uptake blockers (Ofori et al., J Pharmacol Exp Ther. 1989 October; 251(1):258-66). This could lead to secondary local hypoglycemia and a gradual loss of ATP concentrations, as commonly observed in striatal tissue, primary astrocytes and other tissues exposed to MPTP/MPP+(Chan et al., Ann. N.Y. Acad Sci, 1992:648:306-8; Singh et al., Toxicol Appl Pharmacol. 1988 November; 96(2):347-59; Singer et al., Toxicology. 1988 April; 49(1):17-23; Scotcher et al., J Neurochem. 1990 April; 54(4):1295-301; Di Monte et al., J Pharmacol Exp Ther. 1992 April; 261(1):44-9). Other types of brain injury including head trauma, stroke, ischemia and seizure also evoke accumulation of brain/CSF lactate concentrations concomitant to the loss of energy reserves (ie. glycogen and phosphocreatine) and neurological injury (Clausen et al., J Neurosurg. 2005 October; 103(4):597-607; Sacktor et al., J Biol Chem. 1966 Nov. 10; 241(21):5071-5; Chow et al., Arch Dis Child. 2005 November; 90(11):1188-9; Makoroff et al., Pediatr Radiol. 2005 July; 35(7):668-76; Cavus et al., Ann Neurol. 2005 February; 57(2):226-35). These findings suggest that anaerobic glycolysis may be significant factor in the mammalian brain when challenged by various forms of injury, in particular ergogenic challenges to SNc mitochondrial function.

With that, overcoming the initial deficit imposed by PD toxins such as MPP+ are possible with non-glucose intermediates that are capable of sustaining ATP production through substrate level phosphorylation. These compounds should protect against cell death by MPP+, herein also classified under "ANAEROBIC (+)". These constituents should pass through the blood brain barrier (BBB) and augment the function of pyruvate kinase (PK)/lactic acid dehydrogenase (LDH) in order to regenerate the NAD+ required to drive ATP production via phosphoglycerate kinase and pyruvate kinase in glycolysis (Mazzio E A, Soliman K F. Biochem Pharmacol. 2004 Mar. 15; 67(6):1167-84; Mazzio E A, Soliman K F. Neurochem Res. 2003 May; 28(5):733-41; Mazzio et al., Brain Res. 2004 Apr. 9; 1004(1-2):29-44; Mazzio E, Soliman K F Neurotoxicology. 2003 January; 24(1):137-47). Agents capable of mediating positive effects on PK/LDH should in theory offset the metabolic vulnerability imposed by the rise in lactate/pyruvate, nicotinamide adenine dinucleotide (NAD)/nicotinamide adenine dinucleotide reduced (NADH) and NADP/NADPH ratios that occur during hypoglycemia and neurological damage (Auer RN. Metab Brain Dis. 2004 December; 19(3-4):169-75). For this reason, the first component and the base of this nutraceutical formulation are one or more of PYRUVIC ACID (*) (PY), SUCCINIC ACID (SA)* and OXALOACETATE (*) (OA) as well as their corresponding molecular derivatives, analogues, esters or salts. Results from experiments derived in our lab demonstrate that both OA and PY are exceptional substrates for LDH, powerful antioxidants with a capability to protect against MPP+/6-OHDA and $H_2O_2$ toxicities in vitro (Mazzio E, Soliman K F, Neurosci Lett. 2003 Feb. 6; 337(2):77-80, publication in progress). PY/OA are extraordinary in these aspects yeilding a non-toxic combination, which serves as an ergogenic fuel as well as a powerful antioxidant, both playing a fundamental role in PD pathology. SA is also an alternative carboxylic acid with a great propensity to fuel anaerobic glycolysis in the presence of MPP+ (data not published). To date, although these results demonstrate a high probability of therapeutic effects in vivo, there is of current little to no prior art investigative use of PY, OA and SA to treat PD in experimental models. On the other hand, PY can readily enter the brain, serve as a useful substrate for glycolysis, the Krebs cycle and the GABA shunt (Gonzalez et al., J Neurochem. 2005 October; 95(1):284-93) with capability to protect ergogenic failure associated with ischemic stroke and heart disease (Lee et al., J Neurosci. 2001 Oct. 15; 21(20):RC171; Hermann et al., Eur J Heart Fail. 2004 Mar. 1; 6(2):213-8).

The formula next can includes options for vitamin $B_3$±derivates (NIACIN, NIACINAMIDE (*), reduced nicotinamide adenine dinucleotide (NADH) (*), NICOTINIC ACID (*)) which can also protect against MPP+ in vitro, as predictable given the functional role of niacin in sustaining reducing equivalents to drive ATP production through substrate level phosphorylation. A substantial amount of research by others also corroborates our findings and defines a protective role for niacin against PD. First, a niacin deficiency can pre-empt DAergic neuronal degeneration (Williams et al., QJM. 2005 Machr; 98(3):215-26) and MPTP toxicity is associated with a concomitant loss of striatal NAD+/ATP concentrations (Cosi and Marien, Brain Res. 1998 Oct. 26; 809(1): 58-67; Cosi and Marien, Ann N Y Acad Sci. 1999; 890:227-39; Iwashita et al., J Pharmacol Exp Ther. 2004 June; 309(3): 1067-78). In contrast, administration of vitamin $B_3$ derivatives can protect against MPTP toxicity in vivo, an effect thought to be due to preventing the depletion of NAD+ that occurs during apoptotic Poly(ADP-ribose)polymerase-I (PARP-I) activation (Cosi et al., Brain Res. 1996 Aug. 12; 729(2):264-9; Schulz et al., Exp Neurol. 1995 April; 132(2): 279-83; Mukherjee et al., Eur J Pharmacol. 1997 Jul. 2; 330 (1):27-34). Upstream to the loss of intracellular NAD+, the activation of PARP-1 in SNc dopaminergic neurons is under regulatory control of tumor suppressor protein p53, a transcription factor that controls programmed cell death and cell cycle arrest. These events appear to be related, as the administration of vitamin $B_3$ as well as PARP-1/p53 inhibitors or PARP-1 knockout mice equally demonstrate a resistance to MPTP induced SNc neurological injury (Mandir et al., Proc Natl Acad Sci U S A. 1999 May 11; 96(10):5774-9; Mandir et al., J Neurochem. 2002 October; 83(1):186-92; Duan et al., Ann Neurol. 2002 November; 52(5):597-606; Cosi and Marien, Ann N Y Acad Sci. 1999; 890:227-39; Iwashita et al., J Pharmacol Exp Ther. 2004 June; 309(3):1067-78). Niacin also plays a dual protective role against neurodegeneration associated with PD, as it sustains NADPH which is required for the pentose phosphate pathway and removal of $H_2O_2$ (a major contributing factor to PD pathology) through GSH-Px (Williams et al., QJM. 2005 March; 98(3):215-26). While many studies consistently demonstrate a protective role for niacin against SNc degeneration in PD, there has been some skepticism expressed in the literature since its administration may precede formation of N-methylated nicotinamide, a compound structurally similar to MPP+ (Fukushima et al., Asia Pac J Clin Nutr. 2004; 13(Suppl):S176). Nicotinamide N-methyltransferase (NNMT) (as further discussed in the section pertaining to DA oxidative products) can convert pyridines to toxic substances similar in structure to MPP+ (Williams et al., QJM. 2005 March; 98(3):215-26). Therefore, the formulation as described in this embodiment takes this into consideration and niacin could be combined with a balance of natural compound (s) that may slightly downregulate NNMT function. These can include for example, options for plant derived isoquinoline alkaloids (Alston and Abeles, Arch Biochem Biophys. 1988 Feb. 1; 260(2):601-8) such as natural yellow 18 dye/BERBERINE (*) and its containing herb sources, caffeine±precursors (ie. xanthosine and/or its containing herb sources (ie green or cocoa tea) which may compete for methyl groups otherwise donated by s-adenosyl-L-methionine to drive NNMT enzyme activity (Ashihara and Crozier, Trends Plant Sci. 2001 September; 6(9):407-13; Koshiishi et al., FEBS Lett. 2001 Jun. 15; 499(1-2):50-4). As a note, berberine may also contribute additional therapeutic properties as its administration is associated with the reduction of $Ca^{+2}$ mediated neurodegeneration invoked by ROS, brain injury and ischemic tissue damage (Wu et al., Yao Xue Xue Bao. 1997; 32(1):15-8; Zhou et al., Zhongguo Yao Li Xue Bao. 1993 March; 14(2):130-3. Also included will be an adequate amount of MAGNESIUM (Mg) (*) as a slight downregulator of NNMT (Upmeier et al., Arch Biochem Biophys. 1988 May 1; 262(2):445-54).

The addition of Mg to the formulation is highly recommended, as its serves multi-purpose function within this formulation. Magnesium plays a critical role in both the production and utilization of ATP, where it acts as a cofactor for pyruvate kinase and a variety of ATPase pumps that regulate synaptic transmission and membrane voltage. Further, a low dietary intake of Mg correlates with a loss of dopaminergic neurons (Oyanagi, Parkinsonism Relat Disord. 2005 June; 11 Suppl 1:S17-23) and a reduction of Mg brain tissue concentrations are found in human PD patients (Barbiroli et al., Mov Disord. 1999 May; 14(3):430-5). Mg+ can function to augment DA uptake, vesicular storage and transport in particular after neurological insults (Philippu et al., Naunyn Schmiedebergs Arch Pharmacol. 1975 Mar. 25; 287(2):181-90) and $Ca^{+2}$ overload (Schumann and Althoff B, Naunyn Schmiedebergs Arch Pharmacol. 1976 Mar. 24; 293(1):67-74; Baker and Knight J Physiol (Paris). 1980 September; 76(5):497-504), findings which clearly link Mg with the critical loss of ATP requiring processes that are integral to PD pathology. These include both augmenting the function of VMAT2 for sequestration of DA and antagonizing the NMDA receptor which can attenuate excitability in DAergic neurons (Mereu et al., J Neurosci. 1991 May; 11(5):1359-66; Li et al., Neuroscience 1996 March; 71(2):397-410). Mg+ can also offer a diverse range of additional benefits including its ability to antagonize glutamate release, preserve energy substrates (glucose, pyruvate)/energy storage supplies (phosphocreatine), block $Ca^{+2}$ mediated neurotoxicity brought on by other types of ergogenic failure such as cerebral hypoxia/ischemia (Brooks and Kauppinen, Neurochem Int. 1993 November; 23(5):441-50; Lin et al., Life Sci. 2002 Jul. 5; 71(7):803-11), activate CuZn-SOD and prevent the formation of ONOO—, all which are critical to pathological degeneration in PD (Johnson, Medical Hypotheses 2001 56:641-645). Along with Mg, the formulation should incorporate adequate levels of VITAMIN $B_6$ (*) and VITAMIN D (*) being required for its adsorption and utilization. Lastly, the formulation contains other miscellaneous substances found effective in blocking MPP+ toxicity in vitro (not published) via augmenting substrate level production of ATP including but not limited to: A-KETO-CARBOXYLIC ACIDS AND CORRESPONDING SALTS, SHARK CARTILAGE, PHOSPHOENOLPYRUVATE (*), TRYPTOPHAN (*), PYGNOGENOL/GRAPE SEED EXTRACT(*), ALOE VERA (*), ACETYL-L-CARNITINE (*), MANNOSE, FRUCTOSE, FRUCTOSE 1,6 BISPHOSPHATE (*), NARINGEN, RESVERATROL, EGCG, THYMOQUINONE, and/or FDA approved medicinal drugs PIROXICAM—Feldene® (anti-inflammatory agent), DIPYRIMADOLE—Persantine® or NIFEDIPINE (anti-angina drug) Procardia XL™. According to the in vitro screening, these involve an unknown role in potentiation of anaerobic glycolysis (data not published). These medicincal compounds are not nutraceutical agents and carry with them side effects. Therefore, while it is possible to utilize these in a formulation comprised of nutraceutical/medicinal approach—the nutraceutical design of this formulation is for a holistic approach without standard medicines such as that described in (TABLE 2).

KREBS CYCLE/MITOCHONDRIAL FUNCTION/BLOOD DELIVERY OF OXYGEN—The next formula component should pass through the BBB and augment aerobic energy production via oxidative phosphorylation herein also classified under "OXHPHOS (+)". As we have previously reported, RIBOFLAVIN (*), rather than coenzyme $Q_{10}$ appears to exert an important role in the kinetic regulation of complex I and IV function (Mazzio and Soliman, Biochem Pharmacol. 2004 Mar. 15; 67(6):1167-84). Although we found little to no effects for coenzyme $Q_{10}$ on complex I or IV function, riboflavin was capable of potentiating the $V_{max}$ of complex I by approximately 1000% fold, with similar effects on mitochondrial $O_2$ consumption. FLAVIN DERIVATIVES (*) such as flavin adenine dinucleotide (FAD) (*)/flavin mononucleotide (FMN) (*) are well known to regulate aerobic mitochondrial metabolism by mediating redox reactions through the electron transport chain, in particular at complex I-II (which are locations of injury associated with PD) (Sled et al., Biochemistry. 1994 Aug. 23; 33(33):10069-75). And, administration of riboflavin to humans can reverse clinical symptoms associated with mitochondrial myopathy/pathologies (involving complex I-II) as evidenced by a reduction in lactate, restored mitochondrial function and clinical improvement (Bernsen et al., J Neurol Sci. 1993 September; 118(2):181-7; Bar-Meir et al., J Pediatr. 2001 December; 139(6):868-70; Griebel et al., Dev Med Child Neurol. 1990 June; 32(6):528-31; Antozzi et al., Neurology. 1994 November; 44(11):2153-8; Ogle et al., Pediatr. 1997 January; 130 (1):138-45). However, given the potentiation of riboflavin in exacerbating MPP+ toxicity in vitro (Mazzio and Soliman Biochem Pharmacol. 2004 Mar. 15; 67(6):1167-84), further studies will be required and caution should be exercised when including this B vitamin in to the formulation. In contrast, the use of COENZYME $Q_{10}$ (*) (which plays a role in complex I-II function) for treatment of PD has been of considerable interest (Shults et al., Biofactors. 1999; 9(2-4):267-72; Beal, Biofactors. 1999; 9(2-4):261-6) and found effective in antagonizing the effects of MPTP in mice (Schulz et al., Exp Neurol. 1995 April; 132(2):279-83). Our studies indicate coenzyme $Q_{10}$ to be a mild potentiator of complex II function, with no effects on mitochondrial respiration as a whole or protection/exacerbation against MPP+. Therefore, coenzyme $Q_{10}$ may be included into the formulation and since the majority of ATP in the human body is generated by functional mitochondria, the formula will also incorporate constituents required for Krebs cycle function including but not limited to that needed for: pyruvate dehydrogenase complex function—thiamin (VITAMIN B1) (*), LIPOIC ACID (*), pantothenic acid (VITAMIN $B_5$) (*)), gluconeogenesis (BIOTIN (*)) and substances that increase blood, glucose and oxygen delivery to the brain or required for the synthesis of heme (to aid in $O_2$ delivery), herein also classified as "BLOOD FLOW(+)" (GINKO BILOBA (*), vitamin $B_6$, VITAMIN $B_{12}$ (*), Iron (*) and FOLIC ACID (*)).

DUAL FUNCTION FOR FOLATE, VITAMIN $B_6$, VITAMIN $B_{12}$ IN THE MODULATION OF HOMOCYSTEINE METABOLISM—The administration of the micronutrients folic acid, vitamin $B_6$ and vitamin $B_{12}$ serve dual functional roles as these vitamins also regulate homocysteine, in particular via its breakdown to methionine and tetrahydrofolate (Brosnan et al., Acta Biochim Pol. 2004; 51(2):405-13). The administration of these nutrients should attenuate the neurotoxic effects associated with hyperhomocysteinemia, as commonly described in PD pathology, MPTP toxicity and with standard medicinal use of L-Dopa (primary PD drug) (Zoccolella et al., Parkinsonism Relat Disord. 2005 March; 11(2): 131-3; Lamberti et al., Eur J Neurol. 2005 May; 12(5):365-8;

Valkovic et al., Parkinsonism Relat Disord. 2005 June; 11(4): 253-6; (Duan et al., J Neurochem. 2002 January; 80(1):101-10; Muller et al., J Neurol. 2004 September; 251 Suppl 6:VI/44-6). The incorporation of folic acid into the formulation should be in ample quantity as its deficiency can also pre-empt hyperhomocysteinemia and exacerbate the toxic effects of MPTP in animals (Miller, Nutr Rev. 2002 December; 60(12):410-3; Duan et al., J Neurochem. 2002 January; 80(1): 101-10). The administration of vitamin $B_6$ will also be important in terms of homocysteine metabolism, given its ability to antagonize the hyperhomocysteinemic effects of nicotinamide via enhanced methylation (Brosnan et al., Acta Biochim Pol. 2004; 51(2):405-13). For this reason, the formulation should include adequate amounts of folate, niacin and vitamin $B_6$ with additional components: BETAINE (*) and/or SERINE (*) in order to reduce homocysteine levels through aiding in its regulatory conversion to methionine or cysteine, respectively (Yagisawa et al., J Nutr Biochem. 2004 November; 15(11):666-71; Kharbanda et al., Biochem Pharm 2005, in print; Brosnan et al., Acta Biochim Pol. 2004; 51(2):405-13). GARLIC (*) may also be incorporated into the formulation, to further prevent the build up of homocysteine given its ability to stimulate cystathionine β-synthase and inhibit $N_5,N_{10}$-methylenehydrofolate reductase (Yet et al., Nutrition Res. 2005, 25:93-102). Formula components that attenuate homocysteine accumulation are herein also classified under "HOMOCYSTEINE (−)".

ATP STORAGE AND RESERVES—The formulation should next incorporate substances that aid in the storage of ATP herein also classified under "ATP-STORAGE (+)". These include ergogenic substrates: CREATINE (*), PHOSPHOROUS (*) and compounds that augment glucose uptake and use: CHROMIUM salts (*). Disturbances in choline/creatine ratios have been observed in PD pathological models in humans and primates (Brownell et al., Biomed Pharmacother. 1999 April; 53(3):131-40) and creatine protects against MPP+/MPTP, 6-OHDA and glucose deprivation (Andres et al., Neuroscience. 2005; 133(3):701-13; Matthews et al., Exp Neurol. 1999 May; 157(1):142-9; Klivenyi et al., J Mol Neurosci. 2003; 21(3):191-8). Chromium should also be added to the formulation due to its known regulatory role in glucose tolerance, insulin sensitivity (McCarty M F. Med Hypotheses 1980 November; 6(11):1177-89) and glycemic function (McCarty M F, Med Hypotheses. 1999 May; 52(5):401-6). There is enough evidence to support a positive potential role for chromium as a dietary daily component, despite the fact that no alteration in chromium cerebral spinal fluid (CSF) levels have been noted in PD patients (Aguilar et al., J Neural Transm. 1998; 105(10-12):1245-51).

SUMMARY—COMPONENT A. In summary, the very first formula component (COMPONENT A) addresses the loss of ATP/energy failure in the presence of PD model toxins and includes 1) non-glucose compounds capable of augmenting anaerobic glycolysis and substrate level phosphorylation in the presence of MPP+ or rotenone 2) agents that heighten pyruvate+NADH, both of which sustain anaerobic glycolysis and reduce the toxic effects of MPP+ 3) agents that augment oxidative phosphorylation (OXPHOS)/Krebs cycle activity, gluconeogenesis, blood oxidative delivery and dissipate homocysteine accumulation in the brain 4) agents that potentiate whole body glucose metabolism and contribute to ATP storage and reserve and 5) an agent that blocks PARP-1 MPTP induced apoptosis combined with agents that slightly downregulate NNMT.

B. FORMULA COMPONENT B—AGENTS THAT ANTAGONIZE DOPAMINE/6-OHDA TOXICITY, DA AUTO-OXIDATION, SCAVENGE $H_2O_2$, INHIBIT MONOAMINE OXIDASE AND CHELATE IRON—The second most significant contributing factor downstream to the presence of MPP+ appears to be the deleterious effects of ATP loss on DA vesicular storage, destabilized microtubule transport systems for DA synaptic vesicles, rapid accumulation of cytosolic DA and its subsequent massive release from SNc nerve terminals (Chagkutip J et al., Neurochem Res. 2005 May; 30(5):633-9; Ren et al., J Biol Chem. 2005 Oct. 7; 280(40):34105-12; Santos et al., Stroke. 1996 May; 27(5): 941-50; Milusheva et al., Neurochem Int. 1996 May-June; 28(5-6):501-7; Bao et al., J Neurosci. 2005 Oct. 26; 25(43): 10029-40). The nutraceutical components in this section will aim to block these events.

As previously stated, DA is an extremely labile molecule and if not properly sequestered into synaptic vesicles by VMAT2 (where it remains stable under a low pH) can accumulate in the cytosol where it is subject to oxidation yielding a number of DAergic neurotoxins. The three main routes to the oxidation of DA include: 1) enzymatic oxidation via tyrosinase, $PLA_2$/prostaglandin H synthase (COX, peroxidase), lipoxygenase and xanthine oxidase to DA-quinone en route to neuromelanin synthesis 2) enzymatic oxidation by MAO rending formation of $H_2O_2$+DA-aldehydes and 3) non-enzymatic autoxidation of DA by oxygen, $H_2O_2$, other ROS and metals. Any which way, the oxidation of DA (be it non-enzymatic or enzymatic) is thought to be a critical event in directing degenerative pathogenesis in PD including neuronal cell loss, the rampant depletion of glutathione, oxidation of available ascorbate and subsequent massive oxidative stress in the SNc area (Serra et al., J Biol Chem. 2002 Sep. 13; 277(37):34451-61). Formula components in this section will block the deleterious oxidation of DA in the cytosolic compartment through the three main routes.

1. DA OXIDATION TO DA QUINONE—While there are three main routes to the oxidation of DA, the main one is the oxidation to DA quinone (en route through the neuromelanin (NM) pathway) which is central to the pathology of PD (Asanuma et al., Acta Med Okayama. 2004 October; 58(5): 221-33). The neuromelanin pathway originates from the oxidation of DA and if intensified can produce a range of deleterious DA-quinone neurotoxic metabolites such as o-semiquinones or benzothiazolines which are potent inhibitors of aerobic energy metabolism (ie. complex I/Krebs cycle) (Antunes F et al., Toxicology. 2005 Mar. 15; 208(2):207-12; Li HT et al., FEBS J. 2005 July; 272(14):3661-72; Li and Dryhurst, J Neural Transm. 2001; 108(12):1363-74; Smythis and Galzigna, Biochimica et Biophysica Acta (1998) 1380: 159-162). While gradual accumulation of NM in SNc tissue occurs as a natural process of aging (Zecca et al., FEBS Lett. 2002 Jan. 16; 510(3):216-20), an intense heightened concentration of a dark melanized pigment (hyperpigmentation) appears in the SNc and precede neuronal degeneration, alpha-synuclein aggregation, inflammation, oxidative stress, apoptosis (Asanuma et al., Acta Med Okayama. 2004 October; 58(5):221-33; Khan et al., Biochim Biophys Acta. 2005 Jun. 30; 1741(1-2):65-74), Lewy body formation (Halliday et al., Brain. 2005 November; 128(Pt 11):2654-64), depletion of GSH, inhibition of glutamate/dopamine transporters and the loss of tyrosine hydroxylase function (Haid and Lotharius. Exp Neurol. 2005 June; 193(2):279-90). As PD progresses, there is an eventual biphasic loss of NM due to massive oxidation, cell death or its release from dying cells (Garcia-Molina et al., Int J Biochem Cell Biol. 2005 June; 37(6):1179-96). Since NM (as an end product to the pathway) is not toxic itself, but rather protective given its ample ability to sequester iron, free radicals and toxic quinones (Double et al., Neurotoxicol Teratol. 2002 September-October; 24(5):621-8), its ultimate loss presents another major vulnerability to the SNc area.

For these reasons, the formulation should contain constituents that will specifically block the initial oxidation of DA to DA-quinone, or from DA quinone to its toxic metabolites which can be achieved by 1) incorporating inhibitors of prostaglandin $H_2$ synthase (COX/peroxidase), lipoxygenase, $PLA_2$, tyrosinase, xanthine oxidase or antioxidants/metal chelators 2) preventing the enzymatic conversion of dopaminochrome to 5,6,-dihydroxyindole (DT diaphorase inhibitors) 3) blocking the conversion of o-hydroquinones (protective) to o-semiquinones (toxic) via SOD, catalase mimetics (Smythis and Galzigna, Biochimica et Biophysica Acta (1998) 1380:159-162) and 4) inhibiting transglutaminases which otherwise incorporate sulfer amino acids into DA-cysteine conjugate toxic precursors to neuromelanin—herein also referred to as "TRANSGLUTAMINASE-(−)" (cysteamine, CYSTAMINE (*) (Gentile and Cooper A J. Curr Drug Targets CNS Neurol Disord. 2004 April; 3(2):99-104). Animals deficient in enzymes capable of catalytically oxidizing DA to DA-quinone (ie. $PLA_2$ and COX2) exhibit less DAergic neurotoxicity after administration of MPTP (Klivenyi et al., J Neurochem. 1998 December; 71(6):2634-7; Sapirstein and Bonventre Neurochem Res. 2000 May; 25(5):745-53; Feng et al., Neurosci Lett. 2002 Sep. 6; 329(3):354-8; Zhang et al., J Neuropathol Exp Neurol. 2000 January; 59(1):53-61) in a similar manner to those administered COX/(Teismann and Ferger, Synapse. 2001 February; 39(2):167-74; Mohanakumar et al., Brain Res. 2000 May 12; 864(2):281-90; Ferger et al., Naunyn Schmiedebergs Arch Pharmacol. 1999 September; 360(3):256-6; Zhang et al., Food Chemistry. 2006 April; 95(4)579-84; Aubin et al., J Neurochem. 1998 October; 71(4):1635-42) $PLA_2$ inhibitors, which also correspond to the preservation of SNc GSH (Tariq et al., Brain Res Bull. 2001 Jan. 1; 54(1):77-82). These findings suggest the importance of blocking DA oxidation to DA quinone in order to attenuate downstream DA oxidative stress induced nigral degeneration which can be accomplished by one or more of inhibitors of tyrosinase, COX, LOX, $PLA_2$ or xanthine oxidase.

The first of these will include TYROSINASE INHIBITORS—herein also classified as TYROSINASE (−) or polyphenol oxidase (PPO) which is a copper requiring metalloenzyme that catalyzes the oxidation of phenolic compounds into corresponding o-quinones. Heightened tyrosinase activity correlates with elevated risk for PD (Greggio et al., J Neurochem. 2005 April; 93(1):246-56) as well as skin hyper-pigmentation disorders (Boissy et al., Exp Dermatol. 2005 August; 14(8):601-8) and enzymatic browning of fruits and vegetables, all of which can mediate formation of melanized pigments through oxidation of L-DOPA via formation of dopachrome (Galeazzi, Arch Latinoam Nutr. 1984 June; 34(2):269-89; Matheis and Belitz, Z Lebensm Unters Forsch. 1977 Mar. 21; 163(3):191-5). For this reason it has been proposed that the study of food browning via PPO enzymes in vegetables such as potato or mushroom could yield a potentially practical useful tool for the investigation of neurochemical aspects of PD (Henderson et al., Life Sci. 1992; 51(21):PL207-10). Substances that inhibit tyrosinase can include but are not limited to:

| TYROSINASE (−) | |
|---|---|
| Tetrahydroxychalcones (*), Butein (*) | (Khatib et al., J Med Chem. 2005 Jan 17; 13(2): 433-41; Nerya et al., Phytochemistry. 2004 May; 65(10): 1389-95) |
| Prenylated flavonoids, Sanggenon D (*) | (Lee et al., Arch Pharm Res. 2004 Nov; 27(11): 1132-5) |
| Sophoraflavanone G, Kuraridin (*), Kurarinone (*), Norkurarinol | (Kim et al., Biol Pharm Bull. 2003 Sep; 26(9): 1348-50; Son et al., Planta Med. 2003 Jun; 69(6): 559-61) |
| Cinnamic acid (*), Aloin (*) and Sophorcarpidine (*) | (Tan et al., Chin Med J. 2002 Dec; 115(12): 1859-62; Shi et al., Food Chemistry. 2005 Oct; 92(4)707-712) |
| Glabrene/Licorice, licuraside (*), isoliquiritin (*) and licochalcone (*) | (Nerya et al., J Agric Food Chem. 2003 Feb 26; 51(5): 1201-7; Fu et al., J Agric Food Chem. 2005 Sep 21; 53(19): 7408-14) |
| Quercetin (*), Galangin (), Morin (), Fisetin (**), 3,7,4;-trihydroxyflavone, Luteolin, Apigenin, Esculetin (*) | (Xie et al., Biochemistry 2003 Apr; 68(4): 487-91) (Masamoto et al., Biol Pharm Bull. 2004 Mar; 27(3): 422-5) |
| Hexylresorcinol (*), Dodecylresorcinol (*) | (Chen et al., Protein J. 2004 Feb; 23(2): 135-41) |
| Oxyresveratrol (*) | (Shin et al., Biochem Biophys Res Commun. 1998 Feb 24; 243(3): 801-3) |
| Gnetol (*) | (Ohguchi et al., Biosci Biotechnol Biochem. 2003 Mar; 67(3): 663-5) |
| (−)-Epigallocatechin-3-gallate (**), Hinokitiol (*) (beta-thujaplicin), Kojic acid | (Kim et al., Arch Pharm Res. 2004 Mar; 27(3): 334-9; No et al., Life Sci. 1999; 65(21): PL241-6) |
| Reduced glutathione, cysteine, thiol compounds, ascorbic acid, acetic acid | (Gacche et al., J Enzyme Inhib Med Chem. 2004 Apr; 19(2): 175-9; Negishi and Ozawa, Phytochemistry. 2000 Jun; 54(5): 481-7; Nagai and Suzuki, J Agric Food Chem. 2001 Aug; 49(8): 3922-6; Yang et al., J Agric Food Chem. 2001 Mar; 49(3): 1446-9), |
| Dimethylsulfide | (Perez-Gilabert and Garcia-Carmona, Biochem Biophys Res Commun. 2001 Jul 13; 285(2): 257-61) |
| Phytic acid | (Graf et al., Biol Chem. 1987 Aug 25; 262(24): 11647-50), |
| Tannic acid | (Kubo et al., Z Naturforsch 2003 Sep-Oct; 58(9-10): 719-25) |
| Nobiletin | (Sasaki and Yoshizaki, Biol Pharm Bull. 2002 Jun; 25(6): 806-8) |
| Kaempferol | (Kubo and Kinst-Hori, J Agric Food Chem. 1999 Oct; 47(10): 4121-5; Kubo et al., Bioorg Med Chem. 2000 Jul; 8(7): 1749-55) |
| Extract of *hibiscus*, *carex pumila*, and *garcinia subelliptica* | (Masuda et al., Biosci Biotechnol Biochem. 2005 Jan; 69(1): 197-201) |
| Wine phenolics | (Gomez-Cordoves et al., J Agric Food Chem. 2001 Mar; 49(3): 1620-4) |

| TYROSINASE (−) | |
|---|---|
| Green tea | (An et al., Am J Chin Med. 2005; 33(4): 535-46) |
| Procyanidins, Grape seed extract | (Shoji et al., J Agric Food Chem. 2005 Jul 27; 53(15): 6105-11; Yamakoshi et al., Pigment Cell Res. 2003 Dec; 16(6): 629-38) |
| Gallic acid derivatives | (Kubo et al., J Agric Food Chem. 2000 Apr; 48(4): 1393-9) |
| Safflower | (Roh et al., Biol Pharm Bull. 2004 Dec; 27(12): 1976-8) |
| Aisic acid | (Kubo et al., Z Naturforsch] 2003 Sep-Oct; 58(9-10): 713-8) |
| Olive oil constituents | (Kubo and Kinst-Hor, J Agric Food Chem. 1999 Nov; 47(11): 4574-8). |

PGH$_2$ SYNTHASE INHIBITORS—The next constituent includes natural substances that block the initial step of enzymatic DA oxidation to DA quinone through PGH$_2$ SYNTHASE and include but are not limited to COX-1 and COX-2 inhibitors, herein also classified under COX I/II(−):

| COX-1/COX-II (−) | |
|---|---|
| Quercetin (*), Kampferol (*) Chrysin (*) and Galangin (*) | (Kim et al., J Pharmacol Sci. 2004 Nov; 96(3): 229-45; Francis et al., Life Sci. 2004 Dec 24; 76(6): 671-83) |
| Anthocyanins, Delphinidin (), Cyanidin (), Malvidin (**) | (Hou et al., Biomed Biotechnol. 2004; 2004(5): 321-325; Seeram et al., Nutr Cancer. 2003; 46(1): 101-6) |
| Galangin, Morin, Apigenin, Rutin, Catechin, EGCG, Quercetin (*), Chrysin (*), Flavones, Luteolin, Tectorigenin, Bilobetin, Nobiletin, Fisetin, Naringenin, Quercetin, Lonchocarpol, Tomentosanol and Wogonin (*) | (Woo et al., FEBS Lett. 2005 Jan 31; 579(3): 705-11: Kim et al., J Pharmacol Sci. 2004 Nov; 96(3): 229-45; Liang et al., Carcinogenesis. 1999 Oct; 20(10): 1945-52; Raso et al., Life Sci. 2001 Jan 12; 68(8): 921-31; Chi et al., Biochem Pharmacol. 2001 May 15; 61(10): 1195-203) |
| (*) Quercetin, Quercetin 3-glucuronide (*), Quercetin 3'-sulfate (*) and 3'methylquercetin 3-glucuronide | (O'Leary et al., Mutat Res. 2004 Jul 13; 551(1-2): 245-54; Mutoh et al., Jpn J Cancer Res. 2000 Jul; 91(7): 686-91) |
| Ursolic acid (), Eugenol (), Pyrogallol and Cinnamaldehyde | (Huss et al., J Nat Prod. 2002 Nov; 65(11): 1517-21; Subbaramaiah et al., Cancer Res. 2000 May 1; 60(9): 2399-404) |
| Ipriflavone, Resveratrol (*), MSV-60, Amentoflavone, *Ruscus* extract, Notoginseng | (Seaver and Smith, J Herb Pharmacother. 2004; 4(2): 11-8; Murias et al. Bioorg Med Chem. 2004 Nov 1; 12(21): 5571-8) |
| Prenylated flavonoids, Morusin, Kuwanon C, Sanggenon B, Sanggenon D, Kazinol B, Kuraridin (*), Kurarinone (*) and Sophoraflavanone G (*) | (Chi et al., Biochem Pharmacol. 2001 Nov 1; 62(9): 1185-91) |
| Butein (**) and 7,3',4'-trihydroxy flavone | (Selyam et al., Phytother Res. 2004 Jul; 18(7): 582-4) |
| Coumarins, Bergapten | (Yoo et al., Arch Pharm Res. 2002 Dec; 25(6): 824-30) |
| Amentoflavone | (Kim et al., Prostaglandins Leukot Essent Fatty Acids. 1998 Jan; 58(1): 17-24) |
| Oroxylin A | (Chen et al., Biochem Pharmacol. 2000 Jun 1; 59(11): 1445-57) |
| Caffeic acid Phenethyl Ester and *Propolis* | (Rossi et al., Phytomedicine. 2002 Sep; 9(6): 530-5) |

LIPDXYGENASE INHIBITORS—The next constituent includes substances that block the initial step of enzymatic DA oxidation to DA-quinone through inhibition of various forms of lipoxygenase (5-LOX, 12-LOX) herein also referred to as LOX(−) and include but are not limited to:

| LOX (−) | |
|---|---|
| Luteolin (*), Baicalein (*), Fisetin (*), Quercetin (*), Eugenol, Curcumin, Cinnamaldehyde, Piperine, Capsaicin, Allyl sulfide, Oroxylin A, Wogonin | (You et al., Arch Pharm Res. 1999 Feb; 22(1): 18-24; Prasad et al., Prostaglandins Leukot Essent Fatty Acids. 2004 Jun; 70(6): 521-8; O'Prey et al., Biochem Pharmacol. 2003 Dec 1; 66(11): 2075-88; Hsieh et al., Lipids. 1988 Apr; 23(4): 322-6) |
| Morin (*), Galangin (**), Kaempherol (*), Taxifolin (**), EGCG (*), Esculetin (*), Propyl gallate | (Sekiya et al., Biochim Biophys Acta. 1982 Oct 14; 713(1): 68-72; Sadik et al., Biochem Pharmacol. 2003 Mar 1; 65(5): 773-81; Nakadate et al., Gann. 1984 Mar; 75(3): 214-22) |
| Coumarin (*), 7-hydroxy-derivative, Fraxetin (*), Daphnetin (*), Coumarin derivatives (*) | (Fylaktakidou et al., Curr Pharm Des. 2004; 10(30): 3813-33), |
| Amentoflavone (*) | (Kim et al., Prostaglandins Leukot Essent Fatty Acids. 1998 Jan; 58(1): 17-24) |

| LOX (−) | |
|---|---|
| Kuraridin (*), Sophoroflavonone G (*), Kenusanone A (*) Psoralidin (*) 3,5,6,7,3',4'-hexamethoxyflavone, Sinensetin, Nobiletin (), Tangeretin (), Tetramethylscutellarein (), 6,7,8,3',4'-heptamethoxyflavone, Hesperidin (*), Ferulic acid (***) | (Chi et al., Biochem Pharmacol. 2001 Nov 1; 62(9): 1185-91) (Malterud and Rydland, J Agric Food Chem. 2000 Nov; 48(11): 5576-80) |
| Sophoraflavanone G (*), Quercetin (*), Kenusanone A Circiliol (*), Hypolatein (*), Sideritloflavone (*) Silymarin (**) Rhamnetin | (Chi et al., Biochem Pharmacol. 2001 Nov 1; 62(9): 1185-91) (Kim et al., J Pharmacol Sci. 2004 Nov; 96(3): 229-45) (Rui, Mem Inst Oswaldo Cruz. 1991; 86 Suppl 2: 79-85) (Robak et al., Pol J Pharmacol Pharm. 1986 Sep-Dec; 38(5-6): 483-91) |
| Cirsiliol, Hypolaetin, Hypolaetin-8-O-beta-D-glucoside, Gossypetin, Gossypin, Hibifolin, Leucocyanidol | (Ferrandiz et al., Pharmazie. 1990 Mar; 45(3): 206-8; Yoshimoto et al., Biochem Biophys Res Commun. 1983 Oct 31; 116(2): 612-8) |
| Oroxylin A, Baicalein (*), Wogonin Procyanidins Quercetin glycosides | (You et al., Arch Pharm Res. 1999 Feb; 22(1): 18-24) (Schewe et al., J Nutr. 2002 Jul; 132(7): 1825-9) (Luiz et al., Arch Biochem Biophys. 1998 Jan 15; 349(2): 313-20) |
| Entaureidin and 5,3'-dihydroxy-4'-methoxy-7-carbomethoxyflavonol | (Abad et al., Gen Pharmacol. 1995 Jul; 26(4): 815-9) |

PHOSPHOLIPASE $A_2$ INHIBITORS—The next constituent includes substances that block the enzymatic DA oxidation through inhibition of $PLA_2$, herein also referred to as $PLA_2(-)$ which would then further block formation of arachidonic acid as a substrate for prostaglandin synthase (COX). The use of omega-3 fatty acids (ie. canola/fish oil) in this component will aid to divert omega-6 fatty acids (corn oil) from conversion to arachidonic acid via delta-5 desaturase, thereby ultimately reducing $PGE_2$ (a pro-inflammatory prostaglandin associated with PD pathology (Mattammal et al., J Neurochem. 1995 April; 64(4):1645-54). Moreover, vitamin E should be adequately incorporated into the formulation to enhance absorption of omega-3 fatty acids and prevent fatty acid oxidation. $PLA_2$ (−) include but are not limited to:

| $PLA_2$ (−) | |
|---|---|
| Quercetin (), Kaempferol (), Myrecetin (**), Kaempferole-3-galactoside (*), Scutellarein (*), Ochnaflavone (*), Amentoflavone (*), Ginkgetin (*), Isoginkgetin (*), Morelloflavone, Bilobetin, Prenylated flavonoids | (Kim et al., J Pharmacol Sci. 2004 Nov; 96(3): 229-45) |
| Ginkolide (*) | (Zhou et al., Yao Xue Xue Bao. 2001 Feb; 36(2): 92-5) |
| Amentoflavone (*), Ginkgetin (*) | (Kim et al., Prostaglandins Leukot Essent Fatty Acids. 2001 Nov-Dec; 65(5-6): 281-6) |
| Fish oil, Evening primrose oil | (Grataroli et al., Lipids. 1988 Jul; 23(7): 666-70; Grataroli et al., J Lipid Mediat. 1992 Sep; 5(3): 227-36) |
| 2',4',7-trimethoxyflavone | (Han et al., Biol Pharm Bull. 2005 Aug; 28(8): 1366-70) |
| Nobiletin | (Tanaka et al., Biochem Pharmacol. 2004 Aug 1; 68(3): 433-9) |
| Rosmarinic acid | (Ticli et al., Toxicon. 2005 Sep 1; 46(3): 318-27) |
| Omega-3 fatty acids and oils that contain them | (Adam, Eur J Med Res. 2003 Aug 20; 8(8): 381-7) |

XANTHINE OXIDASE INHIBITORS—The next constituent includes substances that block the initial step of enzymatic DA oxidation to DA quinone through inhibition of xanthine oxidase, herein also referred to as XO(−), and include but are not limited to:

| XO (−) | |
|---|---|
| Skull Cap (*) (*Scutellaria baicalensis* (SbE)), Grape seed proanthocyanidins (*) | (Shao et al., Am J Chin Med. 2004; 32(1): 89-95) |
| Hesperitin (), Theaflavin-3,3'-digallate (), Cranberry juice | (Dew et al., J Agric Food Chem. 2005 Aug 10; 53(16): 6510-5; Lin et al., J Agric Food Chem. 2000 Jul; 48(7): 2736-43; Kurisawa et al., Chem Commun. 2004 Feb 7; (3): 294-5) |

| XO (−) | |
|---|---|
| Chrysin (*), Phloretin (*), Luteolin (*), Kaempferol (*), Quercetin (*), Myrecetin (*), Galagin (*), Apigenin (*), Morin, Isorhamnetin, Fisetin (*), Rutin | (Van Hoorn et al., Eur J Pharmacol. 2002 Sep 13; 451(2): 111-8; Selloum et al., Arch Biochem Biophys. 2001 Nov 1; 395(1): 49-56; Nagao et al., Biosci Biotechnol Biochem. 1999 Oct; 63(10): 1787-90; lio et al., J Nutr Sci Vitaminol. 1986 Dec; 32(6): 635-42; Zhu et al., Ethnopharmacol. 2004 Jul; 93(1): 133-40; Moridani et al., Free Radic Biol Med. 2003 Jan 15; 34(2): 243-53) |
| EGCG, 4-t-butylcatechol, Catechin, Fisetin (*), Luteolin (*), Raxifolin | (Moridani et al., Free Radic Biol Med. 2003 Jan 15; 34(2): 243-53; Foppoli et al., Biochim Biophys Acta. 1997 Mar 15; 1334(2-3): 200-6; Asanuma et al., Acta Med. Okayama 2004: 58 (5) 221-233) |
| Quercetin glycosides (*) | (Day et al., Free Radic Biol Med. 2000 Dec 15; 29(12): 1234-43) |
| Apigenin (*), Quercetin (*), Isovitexin | (Lin et al., Biochem Biophys Res Commun. 2002 May 31; 294(1): 167-72) |
| Hydroxyl (*) or Methyl Chalcones (*) (ie 3,3,4,4-tetrahydroxychalcone), Esculetin (*), 4-methylumbelliferone (*) | (Belier and Martin, J Biol Chem. 1951 Oct; 192(2): 831-4) |
| *Propolis*, Caffeic acid phenetyl ester (*), Chrysin (*) and Galangin (*) | (Yoshizumi et al., Yakugaku Zasshi. 2005 Mar; 125(3): 315-21; Russo et al., Fitoterapia. 2002 Nov; 73 Suppl 1: S21-9) |
| (*) 5,7,4'-Trihydroxy-6-methoxyflavone p-coumaric acid derivatives drupanin, 4-acetyl-3,5-diprenylcinnamic acid and trans-ferulic acid O-hexan-3-onyl-ether | (Tapia et al., J Ethnopharmacol. 2004 Dec; 95(2-3): 155-61) |
| Baicalein (*), Wogonin, Baicalin | (Huang et al., Curr Drug Targets Cardiovasc Haematol Disord. 2005 Apr; 5(2): 177-84; Shieh et al., Anticancer Res. 2000 Sep-Oct; 20(5A): 2861-5; Chang et al., Anticancer Res. 1993 Nov-Dec; 13(6A): 2165-70) |
| Pycnogenol, Silymarin (), Silybin (), Silybin flavones (*), Purpurogallin (*) | (Varga et al., Phytomedicine. 2004 Feb; 11(2-3): 206-12; Sheu et al., Anticancer Res. 1998 Jan-Feb; 18(1A): 263-7) |
| Black Tea | (Luczaj and Skrzydlewska Prev Med. 2005 Jun; 40(6): 910-8) |
| Procyanidins, Pygnogenol | (Wang et al., Basic Clin Pharmacol Toxicol. 2004 May; 94(5): 232-7; Packer et al., Free Radic Biol Med. 1999 Sep; 27(5-6): 704-24; Moini et al., J Agric Food Chem. 2000 Nov; 48(11): 5630-9; Moini et al., Adv Exp Med Biol. 2002; 505: 141-9) |
| Anthocyanins, Cyanidin, Cyanidin 3-O-beta-D-glucoside | (Acquaviva et al., Cell Biol Toxicol. 2003 Aug; 19(4): 243-52) |
| Myricetin Glycosides | (Cioffi et al., J Nat Prod. 2002 Nov; 65(11): 1526-9) |

$O_2^-$ SCAVENGERS, AGENTS PROTECTIVE AGAINST XANTHINE/XANTHINE OXIDASE—Along with the previous constituent, $O_2^-$ scavengers and compounds capable of mitigating damage by xanthine/xanthine oxidase induced oxidative stress will also be included, herein also referred to as "Xanthine/XO—$O_2^-$ Scavengers". Substances include but are limited to:

| Xanthine/XO—$O_2$. Scavengers | |
|---|---|
| EGCG (*), EGC (*), Pyrogallol (*), Catechin, Luteolin, Myrecetin, Rutin, Apigenin, Quercetin, Hesperitin, Naringenin, Biochanin, Retinol, Daidzein, Genestein, 4-t-butylcatechol, Taxifolin, Fisetin, Kaempferol, 5,7,4'-trihydroxy-6-methoxyflavone | (Robak and Gryglewski, Biochem Pharmacol. 1988 Mar 1; 37(5): 837-41; Tapia et al., J Ethnopharmacol. 2004 Dec; 95(2-3): 155-61; Moridani et al., Free Radic Biol Med. 2003 Jan 15; 34(2): 243-53; Ignatoy et al., Biosens Bioelectron. 2002 Mar; 17(3): 191-9; Marfak et al., J Agric Food Chem. 2003 Feb 26; 51(5): 1270-7) |
| Caffeic acid (*), Rosmarinic acid (*), Salvianolic acid, Sage | (Yinrong and Yeap, Food Chemistry 2001 75(2), 197-202) |
| Apigenin (*), Quercetin (*), Diosmin | (Beyer and Melzig,, Planta Med. 2003 Dec; 69(12): 1125-9) |
| Green tea polyphenolics, Theaflavin, EGCG (*) | (Kurisawa et al., Chem Commun 2004 Feb 7; (3): 294-5; Park et al., Cell Biol Toxicol. 2003 Oct; 19(5): 325-37; Rah et al., Toxicol Lett. 2005 Feb 15; 155(2): 269-75; Lin et al., J Agric Food Chem. 2000 Jul; 48(7): 2736-43) |
| Scutellarin (**) | (Liu et al., Acta Pharmacol Sin. 2003 Nov; 24(11): 1113-7) |
| Oligomeric proanthocyanidins (*), EGCG (*), Delphinidin, Myrecetin, Gallic acid, Caffeic acid, Fisetin, Quercetin, Catechin, Epicatechin | (Taubert et al., Free Radic Biol Med. 2003 Dec 15; 35(12): 1599-607) |

-continued

| Xanthine/XO—$O_2$. Scavengers | |
|---|---|
| Galangin/Caffeic acid phenethyl ester, *Propolis*, Caffeic (), Chlorogenic acid (), Gallic acid | (Russo et al., Fitoterapia. 2002 Nov; 73 Suppl 1: S21-9; Cheel et al., J Agric Food Chem. 2005 Apr 6; 53(7): 2511-7; Moridani MY and O'Brien PJ, Biochem Pharmacol. 2001 Dec 15; 62(12): 1579-85) |
| Baicalein (*), Baicalin, Morin | (Shieh et al., Anticancer Res. 2000 Sep-Oct; 20(5A): 2861-5; Shi et al., Biochem Mol Biol Int. 1995 Apr; 35(5): 981-94; Toyo'oka et al., Talanta, 2003; 60 (2-3), 467-475) |
| Uric acid | (Stinefelt et al., Ann Clin Lab Sci. 2005 Winter; 35(1): 37-45) |
| Chrysoeriol ± glycoside | (Mishra et al., Bioorg Med Chem. 2003 Jul 3; 11(13): 2677-85) |
| Anacardiaceae spice | (Candan, J Enzyme Inhib Med Chem. 2003 Feb; 18(1): 59-62) |
| Myrecetin, Fisetin and Quercetin | (Ozgova and Hermanek Biochem Pharmacol. 2003 Oct 1; 66(7): 1127-37). |

DT DIAPHORASE, MONOOXYGENASE INHIBITORS—The next section of component B includes substances that block the initial step of enzymatic DA oxidation through providing substances that downregulate DT diaphorase, herein also referred to as "DTD (−)" such as EGCG (Wei et al., Brain Res. 2004 Feb. 27; 999(1):73-80), flavones (Chen et al., Mol Pharmacol. 1995 February; 47(2):419-24) baicalin, oroxylin-A glucoronides (Liu et al., Mol Pharmacol. 1990 June; 37(6):911-5), quercetin (Tamura et al., Jpn J Pharmacol. 1994 August; 65(4):371-3) or mono-oxygenase, herein also referred to as "MO(−)" (ie ASCORBATE (*)/HISTIDINE (*)) (Terland et al., Mol Cell Cardiol. 1997 June; 29(6): 1731-8). The addition of histidine (as a MO(−)) also serves dual purpose as its presence can augment the uptake and transport of ZINC (*) into the brain, where zinc can counteract the pro-oxidant effects of iron as discussed further in the text (Mocchegiani et al., 2005 Progress in Neurobiology 75:367-390). Due to its antioxidant properties, histidine may also be therapeutic for PD given its propensity to protect against oxidative tissue damage by various forms of injury such as iron or ischemia-reperfusion (Kukreja et al., Am J Physiol. 1993 May; 264(5 Pt 2):H1370-81; Obata et al., J Physiol Paris. 1999 May-June; 93(3):213-8) and MPP+ (Obata and Inada, Brain Res. 1999 Jan. 30; 817(1-2):206-8).

2. DA AUTOXIDATION—The second major route for DA oxidation is non-enzymatic autoxidation in the presence of $H_2O_2$, ROS and metals ($Fe^{+2}$, $Cu^{+2}$, and $Mn^{+2}$) (Montgomery et al., Toxicology. 1995 Mar. 31; 97(1-3):3-9; Sayre et al., 1999 Bio-inorganic Chemistry 3:220-225). Autoxidation of DA can render formation of 6-OHDA (a potent neurotoxin) and $O_2.^-$, of which the later if in proximity to nitric oxide (NO) can react to form ONOO—. Peroxynitrite can then re-oxidize DA, deplete available reduced glutathione/ascorbate, incur a substantial loss of endogenous GSH-peroxidase function and destroy the natural ability of GSH to act as an antioxidant, inactivate toxic DA o-semiquinones or ONOO— (Blum et al., 2001; Antunes et al., Toxicology. 2005 Mar. 15; 208(2):207-12). Likewise, the neurological damage associated with PD corresponds to depletion of SNc GSH as consistently evidenced in various studies (Ebadi et al, Prog Neurobiol. 1996 January; 48(1):1-19) and a reduction of GSH (ie. γ-glutamylcysteine. synthetase inhibitor) renders SNc neurons extremely vulnerable to the toxic effects of MPTP and 6-OHDA (Bharath et al., Biochem Pharmacol. 2002 September; 64(5-6):1037-48). In contrast, administration of thiol antioxidants such as dithioreitol, GSH and NAC (which block the autoxidation of DA), prevent MPTP induced toxicity in mice (Annepu and Ravindranath, Neurosci Lett. 2000 Aug. 11; 289(3):209-12; Bahat-Stroomza et al., Eur J Neurosci. 2005 February; 21(3):637-46). For these reasons, the formulation will include substances that prevent non-enzymatic DA oxidation herein classified under "DA-AUTOXIDATION (−)". The compounds chosen were based on their propensity to block DA oxidation to melanized pigments in buffered non-acid solution exposed to atmosphere and corresponding production of ROS upon exposure of $O_2$ (data not published). Of approximately 100 food based compounds tested in our lab, the findings indicate a block of DA oxidation at neutral pH by PY, β-CAROTENE (*), NAC (*), GSH (*), VITAMIN C (*). Given the role of β-carotene in our studies to both scavenge $H_2O_2$ and prevent the oxidation of DA, relative to the lack of effects observed by Vitamin E, it appears that this water soluble vitamin may play a more protective role against PD pathology. The addition of ascorbic acid as a DA-AUTOXIDATION (−) should be limited given its negative counter-indication with iron and 6-OHDA (Mendez-Alvarez et al., Free Radic Biol Med. 2001 Oct. 15; 31(8):986-98). In contrast, ample concentration of thiol substances should be added to the formulation as they are non-toxic, attenuate pathological effects of 6-OHDA, ONOO— and block the formation of DA o-semiquinone neurotoxic radicals (Asanuma et al., Acta Med. Okayama 2004: 58 (5) 221-233).

3. MAO INHIBITION, PEROXIDE SCAVENGERS, ALDEHYDE DEHYDROGENASE POTENTIATION, METAL CHELATORS AND TRACE ELEMENTS—The third major route for DA oxidation is through its enzymatic deamination by MAO A or B. MAO activity increases with aging and can yield toxic products such as hydrogen peroxide ($H_2O_2$), ammonia, aldehydes, reactive oxygen species (Pizzinat et al., 1999, Youdim and Lavie, 1994 and Venarucci et al., 1999), 3,4-dihydroxyphenylacetaldehyde and 3,4-dihydroxyphenylglycolaldehyde. The later two can condense with $H_2O_2$ to form neurotoxic OH radicals (Li et al., 2001 and Tabner et al., 2002). And, DA can directly react with (MAO product) $H_2O_2$ leading to formation of 6-OHDA (neurotoxin) or further condense with (MAO product) acetaldehyde to produce toxic precursors such as 1,2,3,4-tetrahydroisoquinoline, 1,2,3,4-tetrahydro-β-carboline and R-salsolinol which are then subject to methylation (Matsubara et al., Neurotoxicol Teratol. 2002 September-October; 24(5):593-8; Parsons et al., Neurosci Lett. 2003 May 15; 342(1-2):13-6; Naoi et al., Neurotoxicology. 2004 January; 25(1-2):193-204; Matsubara, Nippon Hoigaku Zasshi. 1998 October; 52(5):301-5; Soto-Otero et al., 1998 and Soto-Otero et al., 2001) by nicotinamide, salsolinol and phenylethanolamine N-methyltransferases forming toxic N-methylated pyridines (structurally similar to MPTP/MPP+)(Parsons et al., Neurosci Lett. 2003 May 15; 342(1-2):13-6; Williams et al., QJM. 2005 March; 98(3):215-26; Gearhart et al., Neurochem Int. 2002 June; 40(7):611-20; Naoi et al., Neurotoxicology. 2004 January; 25(1-2):193-204). Due to the importance of MAO activity and the initial condensation reaction between catecholamines and aldehydes that create precursors subject to methylation, the formulation includes substances that 1) inhibit MAO herein also referred to as MAO (−) EGCG (*) and Gromwell Root (*Lithospermum Erythrorhizon*), Shikonins 2) potentiate aldehyde dehydrogenase herein also classified as AD(+) (1.2.1.3) GSH, NAD+(*) 3) downregulate nicotinate/phenylethanolamine N-methyltransferases, herein also referred to as "PNMT (−)" CAFFEINE(*), Mg and 4) scavenge $H_2O_2$.

Hydrogen peroxide plays a very important and central role in PD pathology as it not only oxidizes DA to 6-OHDA but its also reacts directly with 6-OHDA to propagate OH radicals, contributing to the formation of a-synuclein-Fe aggregates/insoluble filaments (Lundvig D et al., Brain Res Mol Brain Res. 2005 Mar. 24; 134(1):3-17: Mandel et al., Brain Res the SNc area vulnerable to oxidative stress and MPTP injury (Klivenyi et al., J Neurosci. 2000 Jan. 1; 20(1):1-7; Zhang et al., Neuropathol Exp Neurol. 2000 January; 59(1):53-61). For these reasons, the formulation includes substances that upregulate endogenous glutathione peroxidase and/or catalase, herein also referred to as "GSH-PX(+)" (NAC (*), GSH(*), SELENIUM (Se) (*), VITAMIN E(*), NADPH(*), curcumin (Biswas et al., Antioxid Redox Signal. 2005 January-February; 7(1-2):32-41). Moreover, the co-administration of niacin (which provides NADPH to drive GSH-Px) along with substances that augment function of GSH-Px should provide synergy in protecting SNc neurons from oxidative stress (Annepu and Ravindranath, Neurosci Lett. 2000 Aug. 11; 289(3):209-12; Bahat-Stroomza et al., Eur J Neurosci. 2005 February; 21(3):637-46). Also included are agents that augment the function of SOD, herein also referred to as SOD (+) (METHIONINE (*), manganese, copper, zinc, PROPOLIS(*)) (Ferrari, Biogerontology 2004 5:275-289), as well as non-enzymatic $H_2O_2$ scavengers, herein referred to as $H_2O_2$ (−), including but not limited to:

| $H_2O_2$ (−) | |
|---|---|
| Morin (*), GSH (*), Pyruvate (*), Carboxylic acids (*), NAC (*), EGCG (*), Caffeic acid (*), Ferulic acid (*), Quercetin (*), Sesamol (*), Carotene (*), Chlorogenic acid (*), myrecetin, rutin, naringin, hesperitin, taxifolin, diosmin, methionine | (Data not shown: Publication in Progress) |
| (*) Acacetin, (*) Dihydrorobinetin, (*) Fisetin, (*) Isorhamnetin, (*) Robinetin, (*) Myricitrin, (*) Hyperoside | (Edenharder et al., Mutat Res. 2003 Sep 9; 540(1): 1-18) |
| Resveratrol (*), Catechin, Gallocatechin | (Yilmaz and Toledo, J Agric Food Chem. 2004 Jan 28; 52(2): 255-60) |
| Pygnogenol (*), Pyrogallol (*), Gallic acid, Anthocyanidins | (Sroka and Cisowski, Food Chem Toxicol. 2003 Jun; 41(6): 753-8; Vanzani et al., J Agric Food Chem. 2005 May 4; 53(9): 3377-82) |
| Gallic acid, Trolox, Kaempferol | (Lopez-Alarcon and Lissi, Free Radic Res. 2005 Jul; 39(7): 729-36) |
| Vanillic/Caffeic acids | (Mansouri et al., J Pharm Biomed Anal. 2005 Sep 1; 39(1-2): 22-6) |
| Baicalein | (Zhao et al., Biochim Biophys Acta. 2004 Nov 18; 1675(1-3): 105-12) |
| Hydroxytyrosol | (O'Dowd et al., Biochem Pharmacol. 2004 Nov 15; 68(10): 2003-8) |

Brain Res Rev. 2005 April; 48(2):379-87). $H_2O_2$ initiates a diverse range of events associated with PD pathology including the activation of mitochondrial toxins via MAO, improper degradation of oxidized proteins through the ubiquitin proteasome pathway and formation of dopachrome, DA quinones and other neurotoxins (Zecca et al., J Clin Pathol: Mol Path 2001 54:414-418; Everse J and Coates P W Free Radic Biol Med. 2005 May 15; 38(10):1296-310; Smythis and Galzigna, Biochimica et Biophysica Acta (1998) 1380:159-162). The role for peroxide in PD pathogenesis is further evidenced by the fact that its removal via potentiation of catalase/SOD prevents injury in MPTP models of injury. Transgenic mice overexpressing cytosolic CuZn-SOD/GSH-Px or the administration of SOD/catalase mimetics (which both dismutase $O_2.^-$, and convert subsequent $H_2O_2$ to water) display similar protection against MPTP, paraquat and 6-OHDA with in vivo models of injury (Peng et al., J Biol Chem. 2005 Aug. 12; 280(32):29194-8; Thiruchelvam, J Biol Chem. 2005 Jun. 10; 280(23):22530-9; Fornai et al., Neurosci Lett. 2002 Jun. 7; 325(2):124-8; Callio et al., J Biol Chem. 2005 May 6; 280(18):18536-42; Ferger et al., Pharmacol Biochem Behav. 2000 March; 65(3):425-31). In contrast, reduction in GSH-Px/CuZn SOD (ie. knockout mice) renders As previously stated, $H_2O_2$ can react with DA to form 6-OHDA which is a potent neurotoxin. 6-OHDA once formed can readily propagate oxidative stress as it is known to reduce striatal zinc and metallothione (antioxidant/metal detoxification agent) and espouse the release of free iron from ferritin, where pro-oxidant effects of iron then predominate (Cuajungco and Lees, Neurobiol Dis. 1997; 4(3-4):137-69; Ebadi et al, Prog Neurobiol. 1996 January; 48(1):1-19; Shiraga et al., Neurochem Int. 1993 December; 23(6):561-6). From our research, we have found that detoxification of 6-OHDA can be achieved by combining cytochrome C with an $H_2O_2$ antioxidant (Mazzio et al., Brain Res. 2004 Apr. 9; 1004(1-2):29-44) and for this reason, also included are compounds that can directly antagonize 6-OHDA toxicity herein also referred to as "6-OHDA (−)" such as NAC, GSH, L-CYSTEINE (*), CYTOCHROME C (*), pyruvate, oxaloacetate, carboxylic acids (Mazzio et al., Brain Res. 2004 Apr. 9; 1004(1-2):29-44), zingerone (Kabuto et al., Neurochem Res. 2005 March; 30(3):325-32) and other substances exerting mild protection such as histidine. Further, substances that are integral constituents of metallothioneine such as serine, LYSINE (*) and cysteine (Cuajungco and Lees, Neurobiol Dis. 1997; 4(3-4): 137-69) are also included. Lysine serves a dual function where its therapeutic utility also serves to block the proliferation of viruses, to which are thought to be involved with the etiology of PD.

IRON CHELATORS—The next constituent of Component B involves the inclusion of substances that chelate iron and/or inhibit heme oxygenase-1 (HO-1). Iron plays a critical role in the initiation and propagation of DA oxidation through various means. Inherently, the substantia nigra, globus pallidus, red nucleus and LC contain of the highest concentration of iron and neuromelanin in the brain, the former of which can initiate oxidation of lipids and proteins and the latter of which is reduced with dopaminergic cell death and the pathogenesis of PD (Vymazal et al., J Neurol Sci. 1995 December; 134 Suppl:19-26; Nicolaus, Med Hypotheses. 2005; 65(4):791-6; Koeppen, J Neurol Sci. 1995 December; 134 Suppl:1-9). Causal factors for the accumulation of free redox active iron and subsequent degeneration of nigral neurons could be disruption of iron regulatory binding proteins (Anderson, J Alzheimers Dis. 2004 December; 6(6 Suppl):S47-52; Yoshida et al., Neurosci Lett. 1995 Apr. 28; 190(1):21-4), genetic defects in genes encoding for iron storage/transport proteins such as ferritin (L/H subunits stabilization:storage/ferroxidase mediated uptake and utilization), caeruloplasmin, iron regulatory protein 2, overexpression of iron uptake transport systems such as lactoferrin/melanotransferrin receptors or the divalent metal transporter-1 (Qian et al., Brain Res Brain Res Rev. 1998 August; 27(3):257-67; Ke and Ming, Lancet Neurol. 2003 April; 2(4):246-53) and relatively low levels of metallothioneine and GSH (both which bind iron) inherent to that area of the brain. The accumulation of iron may also result from the presence of 6-OHDA or glial derived $O_2^-$ both of which can initiate the release of free iron from ferritin (Linert and Jameson, J Inorg Biochem. 2000 April; 79(1-4):319-26). Any which way, the accumulation of redox active free iron is clearly evident in degenerating SNc neurons, surrounding microglia, astrocytes and oligodendrocytes in PD patients and after experimental administration of MPTP/6-OHDA in animals to an extent that parallels elevated HO-1 (an enzyme which yields free $Fe^{+2}$ iron from heme), the disappearance of NM (loss of high affinity binding polymer for $Fe^{+2}$) and degenerative injury (Kaur and Andersen, Ageing Res Rev. 2004 July; 3(3):327-43; Takanashi et al., Parkinsonism Relat Disord. 2001 October; 7(4):311-314; Faucheux et al., Proc Natl Acad Sci U S A. 1995 Oct. 10; 92(21):9603-7; Jiang et al., Sheng Li Xue Bao. 2003 Oct. 25; 55(5):571-6; Zucca et al., Pigment Cell Res. 2004 December; 17(6):610-7; Jiang et al., Sheng Li Xue Bao. 2003 Oct. 25; 55(5):571-6; Watt et al., Nucl. Insir. And Meth. In Phys. Res. B 104(1995) 361-364).

Faulty iron homeostasis in the basal ganglia is dangerous because it can pre-empt DA oxidation, acceleration of a-synuclein protein aggregation (Zhang et al., Biochem Biophys Res Commun. 2005 Jul. 29; 333(2):544-9) and formation of OH radicals which are potent initiators of lipid/protein, DNA and DA oxidation (Bharath et al., Biochem Pharmacol. 2002 September; 64(5-6):1037-48). The presence of $Fe^{3+}$ alone, can mimic the neurotoxic effects of MPTP, SNc cell death and potentiate MPTP loss of striatal DA (Fredriksson et al., Parkinsonism Relat Disord. 2001 April; 7(2):97-105). In contrast, iron deficient rodents are resistant to 6-OHDA and MPTP toxicities (Levenson et al., Exp Neurol. 2004 December; 190(2):506-14; Kaur and Andersen, Ageing Res Rev. 2004 July; 3(3):327-43) and protective effects of iron chelators (ie. cytosine, EGCG, VK-28, clioquincol) are consistently observed in MPTP and 6-OHDA models of PD toxicity (Mandel et al., J Mol Neurosci. 2004; 24(3):401-16; Ferger et al., Eur J Pharmacol. 1998 Nov. 6; 360(2-3):155-63; Kaur et al., Neuron. 2003 Mar. 27; 37(6):899-909). For this reason, nutraceutical substances that reduce/chelate and complex iron, herein also referred to as "FE-C(−)" will be included in the formulation. These include but are not limited to the most powerful substances and herbs as demonstrated in our lab including but not limited to: SESAMOL (*), MORIN (*), CLOVE (*), FERULIC ACID (*), SILYMARIN(*), GREEN TEA (*), ROSEMARY (*), SAGE (*) ellagic acid, PEPPERMINT (*), MYRRH (*), CORRIANDOR (*), CINNAMON (*), quercetin, caffeic acid, ferulic acid and:

| | FE-C (−) |
|---|---|
| Rutin, Morin, Rosemary (*), Sage (*), Oregano (*) (*) Phytic acid, Brown rice bran, Tannic acid | (Caillet et al., Food Chemistry, 2006 article in press) (Ferrari, Biogerontology 2004 5: 275-289) |
| Apigenin, Diosmin, Phloretin, Fisetin, Taxifolin, Naringenin | (van Acker et al., Free Radic Biol Med. 1996; 20(3): 331-42) |
| Quercetin (*), Rutin (*), Myrecetin (*), Luteolin (*), Epicatechin (*), Caffeic acid, Catechin (**), Kaempferol (*), Naringenin, Baicilein | (Brown et al., Biochem J. 1998 Mar 15; 330 (Pt3): 1173-8; Arora et al., Free Radic Biol Med. 1998 Jun; 24(9): 1355-63; Fernandez et al., J Inorg Biochem. 2002 Nov 11; 92(2): 105-11; Cheng and Breen, Biometals. 2000 Mar; 13(1): 77-83; (Aherne and O'Brien, Free Radic Biol Med. 2000 Sep 15; 29(6): 507-14), Mahakunakorn et al., Biol Pharm Bull. 2004 Jan; 27(1): 38-46; Fernandez et al., J Inorg Biochem. 2002 Nov 11; 92(2): 105-11) |
| Theaflavin (*), Theaflavin Digallate | (Yoshida et al., Biochem Pharmacol. 1999 Dec 1; 58(11): 1695-703; O'Coinceanainn et al., J Inorg Biochem. 2004 Apr; 98(4): 657-63) |
| Vitamin E, Zinc (*) | (Fraga and Oteiza e, Toxicology. 2002 Oct 30; 180(1): 23-32) |
| Gallic Acid (*) | (Hynes and Coinceanainn, J Inorg Biochem. 2001 Jun; 85(2-3): 131-42) |
| Silymarin, Silybin (*) | (Borsari et al., J Inorg Biochem. 2001 Jun; 85(2-3): 123-9) |
| Rutin | (Kostyuk and Potapovich, Arch Biochem Biophys. 1998 Jul 1; 355(1): 43-8) |

The accumulation of iron may also involve HO-1 enzyme activity, which can convert heme to free $Fe^{+2}$, carbon monoxide and bile pigments and is significantly expressed in SNc dopaminergic neurons, the nigral neuropil, surrounding reactive astrocytes and Lewy bodies (Schipper et al., Exp Neurol. 1998 March; 150(1):60-8). Upregulation of HO-1 gene expression occurs as a natural response to oxidative stress, or in the presence of DA, cytokines and MPTP, each of which correlates to iron deposition in the nigral area and degenerative SNc lesions. For this reason, also included are agents that inhibit HO-1 directly including but not limited to cysteine, RESEVATROL (*), vitamin C, sulfur compounds (ie. NAC, GSH) (Schipper, Free Radic Biol Med. 2004 Dec. 15; 37(12): 1995-2011), apigenin (Abate et al., Free Radic Biol Med. 2005 Sep. 15; 39(6):711-8), quercetin and kaempferol (Kantengwa and Polla, Biochem Biophys Res Commun. 1991 Oct. 15; 180(1):308-140).

PROTECTIVE ANTIOXIDANT TRACE METALS—While there are adverse effects of reactive metals such as iron in pathology of the basal ganglia, zinc (Zn) and selenium (Se) may offer neuroprotective properties (Zatta et al., 2003 Brain Res Bull 62:15-28; Schweizer et al., Brain Res Rev 2004 45:164-178; Johnson 2001, Medical Hypothesis 56(2): 171-173). For this reason, low doses of Se, Zn and/or manganese should be incorporated into the formulation given their integral roles in the function/expression of endogenous antioxidant enzymes and a demonstrated capacity to antagonize iron-induced, MPTP and 6-OHDA dopaminergic degeneration (Sayre et al., 1999 Bio-inorganic Chemistry 3:220-225; Sziraki et al 1998 Neuroscience 85:1101-1111; Schweizer et al., Brain Res Rev 2004 45:164-178). While zinc is known to exert toxic effects when given at high concentrations, a Zn deficiency is evident in PD patients where low Zn concentrations in cerebrospinal fluid, substantia nigra and caudate nucleus are reported. Furthermore, inflammation can bring on a Zn deficiency due to high requirement for Zn-dependent transcription factors that regulate DNA/nucleic acid synthesis in response to cytokine activation in immunocompentant cells, and condition which is worsened by TNF-a and IL-1 which can then propagate a severe zinc deficiency (ie. hypozincemia) (Caujungco and Lees, Neurobiol Dis. 1997; 4(3-4):137-69; Bush, Curr Opin Chem Biol. 2000 April; 4(2): 184-91). A Zn deficiency can also lead to higher Cu/Zn ratios rending abnormal function of the CuZn SOD enzyme, which turns from an antioxidant to pro-oxidant enzyme, which readily oxidizes (depletes) ascorbate and generates rather than scavenges $O_2.^-$ radicals (Bush, Curr Opin Chem Biol. 2000 April; 4(2):184-91). The administration of zinc can counteract these effects as well as others including Zn mediated a) downregulation of glutamate release, inhibition of NMDA/mGlu-R receptor responses and $Ca^{+2}$ gated ionic channels, protection against NMDA neurotoxicity (excitatory (−)) b) positive modulation on GABA release and inhibitory glycinergic and GABAergic function (inhibitory (+)) c) upregulated gene expression for endogenous antioxidant enzymes and nerve growth factors d) inhibition of nNOS, endonucleases, pro-apoptotic cascades e) augmented synaptic plasticity and f) ability to prevent age related deterioration of learning and memory (Mocchegiani et al., 2005 Progress in Neurobiology 75:367-390). Both Zn and Se can contribute to anti-inflammatory effects through downregulation of MAPK p38, JNK and Nfkappa B DNA binding/AP-1 c Jun activation, where the therapeutic effects of Se also involve its individual ability to augment glutathione peroxidase, reduce lipid peroxidation, increase glucose uptake, ATP production through glycolysis and exert anti-apoptotic effect (Zago et al., Antioxid Redox Signal. 2005 November-December; 7(11-12):1773-82; Zatta et al., 2003 Brain Res Bull 62:15-28). For these reasons, the formulation includes low dose administration of selenium, zinc±manganese. Due to the intricate balance between physiological need for and counter indication of iron or copper, considerable caution should be exercised when considering the inclusion of these metals into the formulation (Bush, Curr Opin Chem Biol. 2000 April; 4(2):184-91; Johnson 2001, Medical Hypothesis 56(2): 171-173).

SUMMARY COMPONENT B: Briefly, the second formula component (COMPONENT B) includes options for inclusion of: 1) substances that prevent the autoxidation of DA to DA-quinone directly or via inhibition of COX/LOX/PPO/$PLA_2$, xanthine oxidase 2) inhibit nicotinamide or phenylethanolamine N-methyltransferase/augment aldehyde dehydrogenase 3) inhibit MAO 4) scavenge $H_2O_2$ 5) reduce/complex/chelate iron 6) antagonize synuclein aggregation (Mg, methionine, vitamin C, GSH, N-acetyl-L-cysteine, NO inhibitors and iron chelators) (Lundvig D et al., Brain Res Mol Brain Res. 2005 Mar. 24; 134(1):3-17; Zhang et al., Biochem Biophys Res Commun. 2005 Jul. 29; 333(2):544-9) 7) antagonize the toxicity of 6-OHDA 8) upregulate endogenous glutathione peroxidase/superoxide dismutase capability 9) inhibit DT diaphorase to block the formation of neurotoxic DA quinone metabolites 10) inhibit HO-1 induction and 11) antagonize the harmful effects of iron by including a balance of antioxidant trace metals.

C. FORMULA COMPONENT C—AGENTS THAT ANTAGONIZE INFLAMMATION, EXCITOTOXICITY AND CA+/PEROXYNITRITE MEDIATED APOPTOSIS—The third issue addressed within this invention is the semi-permanent inflammatory response that occurs in the presence of decaying SNc neurons. Briefly, dopaminergic cell loss, loss of striatal function and the presence of a-synuclein can trigger massive gliosis, microglial activation and proliferation with elevated expression/release of immunological participants such as major histocompatibility antigens, adhesion molecules, COX-2, IL-1b, IL-2, IL-4, IL-6, TNF-alpha, prostaglandins, glutamate, ROS, iNOS, NO and $O_2.^-$ of which the later two can react forming the neurotoxic molecule ONOO— (Kurkowska-Jastrzebska et al., Exp Neurol. 1999 March; 156(1):50-61; Kurkowska-Jastrzebska et al., Acta Neurobiol Exp (Wars). 1999; 59(1):1-8; Ouchi et al., Ann Neurol. 2005 February; 57(2):168-75; Nagatsu and Sawada, Curr Pharm Des. 2005; 11(8):999-1016; McGeer and McGeer Ann N Y Acad Sci. 2004 December; 1035:104-16; Nagatsu et al., J Neural Transm Suppl. 2000; (60):277-90; Sriram et al., FASEB J. 2002 September; 16(11):1474-6; Onyango et al., Mol Cell Neurosci. 2005 March; 28(3):452-61; Hirsch et al., Parkinsonism Relat Disord. 2005 June; 11 Suppl 1:S9-S15; Herbert et al., Neurosci Lett. 2003 Oct. 9; 349(3):191-5; McGeer and McGeer E G, Ann N Y Acad Sci. 2004 December; 1035:104-16; Hald and Lotharius. Exp Neurol. 2005 June; 193(2):279-90; Zhang et al., FASEB J. 2005 April; 19(6):533-42).

The CNS inflammatory response is under the ultimate control of kinases such as tyrosine kinase (Marczin et al., Am J Physiol. 1993 September; 265(3 Pt 2):H1014-8), phosphatidylinositiol 3-kinase (PI3K)/Akt, and mitogen activated protein kinase signaling pathways such as c-Jun NH2-terminal Kinase (JNK), ERK ½ p38 mitogen-activated protein kinase (p38 MAPK) (Kim et al., Pharmacol Res. 2004 May; 49(5): 433-9; O'Callaghan et al., Ann N Y Acad Sci. 1998 May 30; 844:40-9; Willensen et al., Ann N Y Acad Sci. 2002 November 973:237-40; Lee et al., Glia. 2005 Aug. 1; 51(2):98-110; Kuan and Burke, Curr Drug Targets CNS Neurol Disord. 2005 February; 4(1):63-7 (Kao et al., Immunology. 2005 July; 115(3):366-74). MAPK's are evoked by cytokines or inflammatory stimuli, regulated by protein kinase A/cAMP and ultimately regulate gene transcription by phosphorylating nuclear factor-kappa B (NFkappa B) which then bind to the promotor region of gene to initiate transcription for a range of pro-inflammatory proteins (Chio et al., Cell Signal. 2004 May; 16(5):565-75; Lee et al., Life Sci. 2003 Jun. 20; 73(5):595-609; Wang et al., Eur J Neurosci. 2002 December; 16(11):2103-12; Hua et al., J Neuroimmunol. 2002 May; 126(1-2):180-9). Anti-inflammatory agents can antagonize global effects through targeting a number of these signaling routes such as MAPKs, NF-kappaB activation/nuclear translocation or its association with the CREB-binding protein, IkappaB kinase (IKK), activating protein-1 (AP-1) and/or preventing IkappaB degradation or phosphorylation of JNK (Ban et al., Biochem Pharmacol. 2004 Apr. 15; 67(8):1549-57; Wang et al., Drug News Perspect. 2004 December;

17(10):646-54; Saporito et al., Neurochem. 2000 September; 75(3):1200-8; Saporito et al., J Pharmacol Exp Ther. 1999 February; 288(2):421-7). Substances that can inhibit any one of these mechanistic controls can block protein expression or antagonize the formation of iNOS, COX-2, PGE(2) or HO-1 and protect against dopaminergic neuronal loss induced by MPTP (Kurkowska-Jastrzebska et al., Int Immunopharmacol. 2002 July; 2(8):1213-8; Fahrig et al., Mol Pharmacol. 2005 May; 67(5):1544-55; Wu et al., J Neurosci. 2002 Mar. 1; 22(5):1763-71; Du et al., Proc Natl Acad Sci U S A. 2001 Dec. 4; 98(25):14669-74; (Lee et al., Ann N Y Acad Sci. 2004 December; 1030:555-68; Anwar et al., Free Radic Biol Med. 2005 Jul. 15; 39(2):227-36). The co-expression of iNOS and COX-2 could be detrimental as the product formed by NO and $O_2^-$ is ONOO— which plays a highly relevant role in the pathological processes involved with PD. Removal of one or both of $O_2^-$ and NO/ONOO can essentially prevent the deleterious effects of PD model toxins. For example, transgenic mice deficient in iNOS, nNOS, NADPH oxidase or that overexpress Mn/SOD are resistant to the toxicological effects of MPTP or intrastriatal injection of 6-hydroxydopamine (Callio et al., J Biol Chem. 2005 May 6; 280(18):18536-42; Tieu et al., IUBMB Life. 2003 June; 55(6):329-35; Wu et al., Proc Natl Acad Sci U S A. 2003 May 13; 100(10):6145-50; Dehmer et al., Neurochem. 2000 May; 74(5):2213-6; Klivenyi et al., Neurobiol Dis. 1998 October; 5(4):253-8; Andreassen et al., Exp Neurol. 2001 January; 167(1):189-95). Likewise, administration of specific nNOS/iNOS inhibitors or SOD mimetics can protect against the neurotoxicity of MPTP (Klivenyi et al., Neuroreport. 2000 Apr. 27; 11(6):1265-8; Levites et al., J Neurochem. 2001 September; 78(5):1073-82; Kurosaki et al., Neurol Res. 2002 October; 24(7):655-62; Choi et al., Neurotoxicology. 2002 September; 23(3):367-74 (Peng et al., J Biol Chem. 2005 Aug. 12; 280(32):29194-8). In brief summary, the anti-inflammatory component will include natural substances that downregulate or inactivate phosphorylated MAPK's such as ERK ½ kinase, p38 MAPK, c-jun N-terminal kinase (JNK), inhibit IkappaB kinase, IkappaB degradation, NF-kappaB, AP-1 activation, antagonize COX-2/PGE2/iNOS and reduce expression of TNF-alpha and other pro-inflammatory proteins in immuno-competent cells, herein also classified under "MAPK/NF-KAPPA-B/iNOS/COX-2(−)".

| MAPK/NF-KAPPA-B/iNOS/COX-2 (−) | |
|---|---|
| Selenium (*), Zinc (*) | (Zatta et al., 2003 Brain Res Bull 62: 15-28; (Zago et al., Antioxid Redox Signal. 2005 Nov-Dec; 7(11-12): 1773-82). |
| Chrysin (*), Quercetin (*), Galangin, *Propolis* or its derivatives | (Blonska et al., J Ethnopharmacol. 2004 Mar; 91(1): 25-30) (Cho et al., Pharmacol Res. 2004 Jan; 49(1): 37-43; Chen et al., Eur J Pharmacol. 2005 Oct 3; 521(1-3): 9-20; Martinez-Florez et al., J Nutr. 2005 Jun; 135(6): 1359-65; Jung and Sung, Biofactors. 2004; 21(1-4): 113-7; Cho et al., Mol Cell Biochem. 2003 Jan; 243(1-2): 153-60) |
| Apigenin (*) | (van Meeteren et al., Biochem Pharmacol. 2004 Mar 1; 67(5): 967-75; Scuro et al., BMC Biochem. 2004 Apr 21; 5:5) |
| Luteolin (*) | (Hu and Kitts Mol Cell Biochem. 2004 Oct; 265(1-2): 107-13; Kim et al., Arch Pharm Res. 2004 Sep; 27(9): 937-43; van Meeteren et al., Biochem Pharmacol. 2004 Mar 1; 67(5): 967-75) |
| Diosmetin (*), 3-hydroxyflavone (*), Pillion (*), 4'7'-dihydroxyflavone (*), Ayanin (*), Luteolin (*), Tectochrysin (*), 3',4'-dihydroxyflavone (*), Tamarixetin, Genestein, Kaempferol, Izalpinin, Ombuine, Biochanin, Tectorigenin, Daidzein, 7-hydroxyflavone, Rhamnetin, flavone, EGCG, Mearnsetin, Liquiritigenin, Myrecetin | (Matsuda et al., Bioorg Med Chem. 2003 May 1; 11(9): 1995-2000) |
| Hydroxychalcones (*) | (Ban et al., Biochem Pharmacol. 2004 Apr 15; 67(8): 1549-57; Rojas et al., Schmiedebergs Arch Pharmacol. 2003 Sep; 368(3): 225-33; Ko et al., Bioorg Med Chem. 2003 Jan 2; 11(1): 105-11), |
| EGCG (*)/green tea | (Chiu and Lin, J Agric Food Chem. 2005 Sep 7; 53(18): 7035-42; Sutherland et al., FASEB J. 2005 Feb; 19(2): 258-60; Singh et al., Arthritis Rheum. 2002 Aug; 46(8): 2079-86), |
| Butein (*) | (Lee et al., Biochem Biophys Res Commun. 2004 Oct 8; 323(1): 125-32), |
| Anthocyanins (*) | (Hou et al., Biomed Biotechnol. 2004; 2004(5): 321-325; Sauebin et al., Planta Med. 2004 Aug; 70(8): 745-52), |
| 5,6,3',5'-tetramethoxy 7,4'-hydroxyflavone, *Artemisia Absinthium*, Wormwood, Blackwalnut (*) | (Lee et al., Ann N Y Acad Sci. 2004 Dec; 1030: 555-68), |
| Scutellarin (**) | (Liu et al., Pharmacol Res. 2005 Mar; 51(3): 205-10) |
| Isovitexin (**) | (Lin et al., Planta Med. 2005 Aug; 71(8): 748-53). |
| Naringin (**), Hesperitin and Naringenin | ((Sakata et al., Cancer Lett. 2003 Sep 25; 199(2): 139-45; Kanno et al., Life Sci. 2005 Aug 30; [Epub ahead of print; Lin et al., J Cell Physiol. 2005 Feb; 202(2): 579-90), |
| Baicalein (**) | (Chen et al., Biochem Pharmacol. 2004 Mar 1; 67(5): 957-65; Lin et al., Biochem Pharmacol. 2003 Nov 1; 66(9): 1821-32), |
| Silibinin, Silymarin (**) | (Schumann et al., J Hepatol. 2003 Sep; 39(3): 333-40; Wang et al., Eur J Neurosci. 2002 Dec; 16(11): 2103-12; Kang et al., J Pharmacol Exp Ther. 2002 Jul; 302(1): 138-44), |
| Amentoflavone | (Banerjee et al., Prostaglandins Leukot Essent Fatty Acids. 2002 May-Jun; 66(5-6): 485-92), |
| Licorice extract or its constituents | |
| Wogonin | (Takahashi et al., Cancer Sci. 2004 May; 95(5): 448-53), |
| Curcumin, Luteolin, Wognonin, Kaempferol, Nobiletin, Bilobetin | (Lee et al., FASEB J. 2003 Oct; 17(13): 1943-4), (Kim et al., J Pharmacol Sci. 2004 Nov; 96(3): 229-45). |

Additionally, phosphodiesterase (PDE) inhibitors, in particular PDE 1 and IV will be included due to synergist positive effects that cAMP has on increasing endothelial NOS (which enhances vasodilation and blood circulation), downregulating iNOS (Markovic et al., Curr Drug Targets Inflamm Allergy. 2003 March; 2(1):63-79) and protecting against MPTP toxicity (Hulley et al., Eur J Neurosci. 1995 Dec. 1; 7(12):2431-40).

| PDE (−) | |
|---|---|
| Butein (*) | (Yu et al., Eur J Pharmacol. 1995 Jun 23; 280(1): 69-77) |
| Cirsimarin (*) | (Girotti et al., Planta Med. 2005 Dec; 71(12): 1170-2) |
| Grape Skins (*), Anthocyanin (*), Malvidin (*) | (Dell'Agli et al., J Agric Food Chem. 2005 Mar 23; 53(6): 1960-5) |
| Diosmetin (*), Luteolin (*), Apigenin, Quercetin, Myrecetin | (Ko et al., Biochem Pharmacol. 2004 Nov 15; 68(10): 2087-94) |
| (+)-Catechin (*), Caffeic acid (*) | (Paliyath and Poovaiah. Plant Cell Physiol. 1985; 26(1): 201-9) |
| Gingko Biloba extract | (Campos-Toimil et al., Arterioscler Thromb Vasc Biol. 2000 Sep; 20(9): E34-40) |
| Biochanin A, Tyrphostin, Diadzein (*) | (Nichols and Morimoto, Mol Pharmacol. 2000 Apr; 57(4): 738-45) |
| Theophylline | (Satake et al., Eur J Pharmacol. 1999 Jul 21; 377(2-3): 193-7) |
| Amentoflavone (*), Bilobetin (*), sequoiaflavone, Ginkgetin, Isoginkgetin | (Saponara and Bosisio.E.J Nat Prod. 1998 Nov; 61(11): 1386-7) |
| Scutellarein (*), Phloretin (*), Naringenin | (Kuppusamy and Das, Biochem Pharmacol. 1992 Oct 6; 44(7): 1307-15; Orallo et al., Planta Med. 2005 Feb; 71(2): 99-107) |

This invention also leaves open the option to include agents that augment endogenous production or function of GABA/GABA receptors under (GLUergic (−)/GABAergic (+)) and directly antagonize excitotoxicity (ie. Zn, TAURINE (*), GLYCINE (*)). And, since MPP+ espouses a reduction of BH4 rendering nNOS to release greater quantity of $O_2.^-$ (Shang et al., Biol Chem. 2004 Apr. 30; 279(18):19099-112), and optional BIOPTERIN (*) into the formulation.

SUMMARY COMPONENT C. Briefly, the third formula component (COMPONENT C) includes substances that: 1) downregulate CNS inflammation 2) inhibit iNOS, tyrosine kinase 3) augment cAMP 4) inhibit JNK/p38 MAPK 5) upregulate I kappa B alpha or inhibit NF-KappaB activation or promotor activity in the regulation of pro-inflammatory protein expression 6) augment glutamine synthetase or glia glutamate uptake 7) antagonize $Ca^{+2}$ mediated and/or excitotoxicity 8) scavenge ONOO— or $O_2.^-$ 8) inhibit angiotensin converting enzyme and 9) inhibit PDE.

The formula as presented in the tables below also include corresponding ligands, salt forms, analogues, glycosides, precursor compounds or alternative concentrated food/herbs sources containing desired compounds as to therapeutically treat/prevent the progression of Parkinson's disease or for any other clinically beneficial results. Optional concentrated food/plant sources containing the desired flavonoids as discussed in each mechanism above are included in the TABLE 1 below as determined from (1) United States Department of Agriculture—Phytochemical Databases (2) Dr. Duke's Phytochemical and Ethnobotanical Database (3) Phytotherapies.org (4) Justesen J Chromatogr A. 2000 Dec. 15; 902(2):369-79 (5) Hoffmann D. Herbal Material Medica (www.healthy.net) and (6) Center for New Crops & Plant Products (NewCROP) at Purdue University. In TABLE 1, the components as they first appear are listed with target and therapeutic ranges, followed by an (") if duplicated under another category. The formulation is comprised largely of available substances, and therapeutic administrative ranges are displayed as estimated daily intake for humans in the example of TABLE 2.

TABLE 1

Parkinsons Nutraceutical Formulation/Options for Constituent by Mechanism & Constituent by Plant Source

| Serving Size 1<br>Amount Per Serving<br>Formula Constituent | Target | Opt Range | Unit |
|---|---|---|---|
| (Base Fat Soluble Vitamins (+)) | | | |
| Vitamin A (ie. Beta-Carotene; Retinyl Acetate) | 5000 | 0-15000 | IU |
| Vitamin D (ie. Cholecalciferol) | 400 | 0-600 | IU |
| Vitamin E (ie. Alpha Tocopheryl Acetate) | 300 | 0-600 | IU |
| Vitamin K (Phytonadione) | 80 | 0-120 | mcg |
| (ANAEROBIC (+)) | | | |
| Pyruvic acid (ie. Sodium Pyruvate) - Base Constituent | 1500 | 0-10000 | mg |
| Oxaloacetate (ie. Sodium Oxaloacetate) - Base Constituent | 150 | 0-10000 | mg |

TABLE 1-continued

Parkinsons Nutraceutical Formulation/Options for Constituent by Mechanism & Constituent by Plant Source Serving Size 1
Amount Per Serving

| Formula Constituent | Target | Opt Range | Unit |
|---|---|---|---|
| Succinic Acid (ie. Sodium Succinate) - Base Constituent | 150 | 0-10000 | mg |
| Vitamin B-3 (Nicotinamide)/ | 350 | 0-3000 | mg |
| Malic Acid (ie. Sodium Malate) | 10 | 0-3000 | mg |
| NADH+ | 750 | 0-750 | mg |
| Magnesium (ie. Magnesium Oxide) | 300 | 0-3000 | mg |
| *Aloe Vera* (25 mg of *Aloe Vera* 200: 1 extract, equivalent to 5 g Fresh *Aloe Vera*) | 20 | 0-400 | mg |
| Acetyl-L-Carnitine (ie. Hydrochloride) | 250 | 0-3000 | mg |
| Phosphoenolpyruvate | 10 | 0-1000 | mg |
| Tryptophan | 125 | 0-2000 | mg |
| Fructose, 1,6-Bisphosphate, Mannose/Fructose | 100 | 0-3000 | mg |
| Shark Cartiladge | 10 | 0-500 | Mg |
| Pycnogenol/(*Pinus Maritima*, Canadian Spruce, Grape Seeds: Extract, Powder, Concentrate) | 20/100 | 0-200/0-2000 | mg |
| Naringin/(Orange, Grapefruit: Extract, Powder, Concentrate) | 20/100 | 0-200/0-2000 | mg |
| Resveratrol | 970 | 0-300 | mg |
| Medicinal Agents (Piroxicam, Nifedipine, Dipyridamole) | N/A | | |
| Thymoquinone (Black Cumin Seed) | 150 | 0-500 | Mg |
| (OXPHOS (+)) | | | |
| Riboflavin (Vitamin B-2) | 25 | 0-600 | Mg |
| FAD/FMN | 25 | 0-300 | Mg |
| Coenzyme Q10 | 30 | 0-1000 | Mg |
| Thiamin | 100 | 0-400 | Mg |
| Alpha-Lipoic Acid | 50 | 0-2000 | Mg |
| Pantothenic Acid (ie. Calcium Pantothenate) | 100 | 0-400 | Mg |
| Biotin | 300 | 0-1200 | μg |
| (BLOOD FLOW (+)/HOMOCYSTEINE (−)) | | | |
| *Ginko Biloba* (Extract, Powder, Concentrate) | 50 | 0-2000 | Mg |
| Pyrodoxine HCL (Vitamin B-6) | 400 | 0-2000 | Mg |
| Vitamin B12 (Cyanocobalamin) | 100 | 0-350 | μg |
| Folic Acid | 800 | 0-3000 | μg |
| L-Serine | 100 | 0-400 | Mg |
| Betaine Hydrochloride/(Beets: extract powder concentrate) | 75/100 | 0-350/0-2000 | Mg |
| Garlic: (Extract, Powder, Concentrate) | 100 | 0-2000 | Mg |
| (ATP-STORAGE (+)) | | | |
| Chromium Picolinate | 75 | 0-250 | μg |
| Phosphorous | 50 | 0-300 | Mg |
| Creatine (ie. Monohydrate or Pyruvate) | 200 | 0-3000 | Mg |
| (TRANSGLUTAMINASE (−)) | | | |
| Cystamine | 50 | 0-50 | Mg |
| (DA-AUTOXIDATION (−)) | | | |
| Ascorbic Acid | 50 | 0-2000 | Mg |
| L-Cysteine | 100 | 0-1000 | Mg |
| N-Acetyl-L-Cysteine | 500 | 0-2000 | Mg |
| L-Glutathione | 250 | 0-2000 | Mg |
| (TYROSINASE (−)) | | | |
| Esculetin/(Dill, Tarragon, Carrot, Basil, Blueberry: Extract, Powder, Concentrate) | 20/100 | 0-200/0-2000 | Mg |
| Tetrahydroxychalcones | 10 | 0-250 | Mg |
| Sanggenon D | 10 | 0-250 | Mg |
| Kuraridin/Kurarinone/(Narrowleaf Sophora: Extract, Powder, Concentrate) | 20/100 | 0-200/0-2000 | Mg |
| Quercetin ± glucosides/(Black Tea, Green Tea, Lovage Leaves, Evening Primrose, Mayapple, *Matricaria recutita* (chamomile), *Trifolium pratense* (red clover), *Althaea officinalis* (marshmallow), *Hypericum perforatum* (St john's Wort): Extract, Powder, Concentrate) | 20/100 | 0-200/0-2000 | Mg |
| Cinnamic Acid/(Grape, Thyme, Rhubarb, Fennel, Cilantro, Green Tea, *Propolis*: Extract, Powder, Concentrate) | 20/100 | 0-200/0-2000 | Mg |
| Resveratrol/(Grapes, Mulberries: Extract, Powder, Concentrate) | 20/100 | 0-200/0-2000 | Mg |
| Butein/(*Rhus verniciflua* Stokes, *Faba* beans: Extract, Powder, Conc) | 20/100 | 0-200/0-2000 | Mg |
| Aloin/(*Aloe Vera*: Extract, Powder, Concentrate) | 20/100 | 0-200/0-2000 | Mg |
| Sophorcarpidine | 10 | 0-250 | Mg |
| Licorice extract | 100 | 0-2000 | Mg |
| Licuraside/Licochalcone | 10 | 0-250 | Mg |

TABLE 1-continued

Parkinsons Nutraceutical Formulation/Options for Constituent by Mechanism & Constituent by Plant Source Serving Size 1
Amount Per Serving

| Formula Constituent | Target | Opt Range | Unit |
|---|---|---|---|
| Gallic Acid/(Green Tea, Mango, Rhubarb, Cranberry: Extract, Powder, Concentrate) | 20/100 | 0-200/0-2000 | Mg |
| Isoliquiritin/(Licorice: Extract, Powder, Concentrate) | 20/100 | 0-200/0-2000 | Mg |
| Resorcinol/(White Bulberry: Extract, Powder, Concentrate) | 20/100 | 0-200/0-2000 | Mg |
| (COX I/II (−)) | | | |
| Chrysin/(Carrot, Sour Cherry, Skullcap: Extract, Powder, Concentrate) | 20/100 | 0-200/0-2000 | Mg |
| Quercetin ± glucosides/(Black Tea, Green Tea, Lovage Leaves, Evening Primrose, Mayapple, *Matricaria recutita* (chamomile: Extract, Powder, Concentrate), *Trifolium pratense* (red clover: Extract, Powder, Concentrate), *Althaea officinalis* (marshmallow: Extract, Powder, Concentrate), *Hypericum perforatum* (St john's Wort: Extract, Powder, Concentrate): Extract, Powder, Concentrate) | " | " | " |
| Galangin/(Licorice, Siamese Ginger: Extract, Powder, Concentrate) | 20/100 | 0-200/0-2000 | Mg |
| Kuraridin/Kurarinone/(Narrowleaf Sophora: Extract, Powder, Concentrate) | " | " | " |
| Sophoraflavonone | " | " | " |
| Resveratrol/(Grapes, Mulberries: Extract, Powder, Concentrate) | " | " | " |
| Wogonin/(Skullcap: Extract, Powder, Concentrate) | 20/100 | 0-200/0-2000 | Mg |
| Kaempferol/(Black Tea, Green Tea, Capers, Dill: Extract, Powder, Concentrate) | 20/100 | 0-200/0-2000 | Mg |
| Anthocyanins/Proanthocyanidin/(Açai, blackcurrant, chokeberry, orange, blackberry, black raspberry, raspberry, wild blueberry, cherry, red currant, red grape, red wine, seed coat of black soybean (*Glycine max* L. Merr.), black chokeberry, bilberry, *cacao* beans, *sorghum* and cinnamon.: Extract, Powder, Concentrate) | 20/100 | 0-200/0-2000 | Mg |
| (LOX (−)) | | | |
| (Luteolin/(Thyme, Parsely, Peppermint, Celery Seed, Chamomile, Rosemary, Fenugreek and *Ginko Biloba*: Extract, Powder, Concentrate) | 20/100 | 0-200/0-2000 | Mg |
| Baicalein *Scutellaria baicalensis* (Baical Skullcap: Extract, Powder, Concentrate) | 20/100 | 0-200/0-2000 | Mg |
| Fisetin/(*Acacia*: Extract, Powder, Concentrate) | 20/100 | 0-200/0-2000 | Mg |
| Quercetin ± glucosides/(Black Tea, Green Tea, Lovage Leaves, Evening Primrose, Mayapple, *Matricaria recutita* (chamomile: Extract, Powder, Concentrate), *Trifolium pratense* (red clover: Extract, Powder, Concentrate), *Althaea officinalis* (marshmallow: Extract, Powder, Concentrate), *Hypericum perforatum* (St john's Wort: Extract, Powder, Concentrate): Extract, Powder, Concentrate) | " | " | " |
| Morin/(White Bulberry: Extract, Powder, Concentrate) | 20/100 | 0-200/0-2000 | Mg |
| Kaempferol/(Black Tea, Green Tea, Capers, Dill: Extract, Powder, Concentrate) | " | " | " |
| EGCG/(Green Tea, Oolong Tea, Black Tea: Extract, Powder, Concentrate) | 20/100 | 0-200/0-2000 | Mg |
| Esculetin/(Dill, Tarragon, Carrot, Basil, Blueberry,: Extract, Powder, Concentrate) | " | " | " |
| Coumarin/(Celery Seed, Meadowsweet, Chamomile: Extract, Powder, Concentrate) | 20/100 | 0-200/0-2000 | " |
| Fraxetin | 0 | 0-250 | Mg |
| Daphnetin/(Chickpea: Extract, Powder, Concentrate) | 20/100 | 0-200/0-2000 | Mg |
| Sophoraflavone G | 0 | 0-250 | Mg |
| Amentoflavone/(*Ginkgo biloba*: Extract, Powder, Concentrate) | 20/100 | 0-200/0-2000 | Mg |
| Kuraridin | " | " | " |
| Kenusanone A | 10 | 0-250 | Mg |
| Psoralidin | 10 | 0-250 | Mg |
| Hypolatein | 10 | 0-250 | Mg |
| Sideritloflavone | 10 | 0-250 | Mg |
| Silymarin, Silybin (Milk Thistle: Extract, Powder, Concentrate) | " | " | " |
| (PLA2 (−)) | | | |
| Kaempferol/(Black Tea, Green Tea, Capers, Dill: Extract, Powder, Concentrate) | " | " | " |
| Scutelarein/(Skullcap: Extract, Powder, Concentrate) | 20/100 | 0-200/0-2000 | Mg |
| Ochnaflavone | 10 | 0-250 | Mg |
| Amentoflavone/(*Ginkgo biloba*: Extract, Powder, Concentrate) | " | " | " |
| Isoginkgetin/(*Ginko Biloba*: Extract, Powder, Concentrate) | 20/100 | 0-200/0-2000 | Mg |
| Ginkolide/(*Ginko Biloba*: Extract, Powder, Concentrate) | 20/100 | 0-200/0-2000 | Mg |
| Ginkgetin/(*Ginko Biloba*: Extract, Powder, Concentrate) | " | " | " |
| Omega - fatty acids (fish oil, rape seed, canola oil) | 300 | 0-1500 | Mg |
| Evening Primrose Oil | 250 | 0-1500 | Mg |
| Cyanidins/(Elderberry, Cherries, Raspberries: Extract, Powder, Concentrate) | 250 | 0-500 | Mg |

TABLE 1-continued

Parkinsons Nutraceutical Formulation/Options for Constituent by
Mechanism & Constituent by Plant Source Serving Size 1
Amount Per Serving

| Formula Constituent | Target | Opt Range | Unit |
|---|---|---|---|
| (XO (−)) | | | |
| Chrysin/(Carrot, Sour Cherry, Skullcap: Extract, Powder, Concentrate) | " | " | " |
| Phloretin/(Rosaceae Apple: Extract, Powder, Concentrate) | 20/100 | 0-200/0-2000 | Mg |
| Luteolin/(Thyme, Parsely, Peppermint, Celery Seed, Chamomile, Rosemary, Fenugreek and *Ginko Biloba*: Extract, Powder, Concentrate) | " | " | " |
| Kaempferol/(Black Tea, Green Tea, Capers, Dill: Extract, Powder, Concentrate) | " | " | " |
| Quercetin ± glucosides/(Black Tea, Green Tea, Lovage Leaves, Evening Primrose, Mayapple, *Matricaria recutita* (chamomile: Extract, Powder, ç Concentrate), *Trifolium pratense* (red clover: Extract, Powder, Concentrate), *Althaea officinalis* (marshmallow: Extract, Powder, Concentrate), *Hypericum perforatum* (St john's Wort: Extract, Powder, Concentrate): Extract, Powder, Concentrate) | " | " | " |
| Myricetin/(Green Tea, Black Tea, Fennel, Parsley: Extract, Powder, Concentrate) | 20/100 | 0-200/0-2000 | mg |
| Galangin/(Licorice, siamese ginger: Extract, Powder, Concentrate) | " | " | " |
| Apigenin/(Dried Parsely, Chamomile, Celery Seed: Extract, Powder, Concentrate) | 20/100 | 0-200/0-2000 | mg |
| Fisetin/(*acacia*: Extract, Powder, Concentrate) | " | " | " |
| Hydroxyl or methyl chalcones | 10 | 0-250 | mg |
| Silymarin, Silybin (Milk Thistle: Extract, Powder, Concentrate) | 20/100 | 0-200/0-2000 | mg |
| Ferulic Acid/(Pineapple, Dill, Orange, Grapefruit, Lemon, *Angelica sinensis* (dong quai: Extract, Powder, Concentrate), *Melissa officinalis* (lemon balm: Extract, Powder, Concentrate) | " | " | " |
| (XANTHINE OXIDASE XO/O$_2$ (−)) | | | |
| EGCG/(Green Tea, Oolong Tea, Black Tea: Extract, Powder, Concentrate) | " | " | " |
| Apigenin/(Dried Parsely, Chamomile, Celery Seed: Extract, Powder, Concentrate) | " | " | " |
| Chlorogenic acid (Coffee, Sunflower seeds, Blueberry, Bilberry: Extract, Powder, Concentrate) | 20/100 | 0-200/0-2000 | mg |
| Quercetin ± glucosides/(Black Tea, Green Tea, Lovage Leaves, Evening Primrose, Mayapple, *Matricaria recutita* (chamomile: Extract, Powder, Concentrate), *Trifolium pratense* (red clover: Extract, Powder, Concentrate), *Althaea officinalis* (marshmallow: Extract, Powder, Concentrate), *Hypericum perforatum* (St john's Wort: Extract, Powder, Concentrate): Extract, Powder, Concentrate) | " | " | " |
| Diosmin/(Hyssop, Rosemary: Extract, Powder, Concentrate) | 20/100 | 0-200/0-2000 | mg |
| Baicalein *Scutellaria baicalensis*/(Baical Skullcap: Extract, Powder, Concentrate) | " | " | " |
| Rosmarinic Acid/(Rosemary: Extract, Powder, Concentrate) | 20/100 | 0-200/0-2000 | mg |
| Delphinidin/(Blueberries: Extract, Powder, Concentrate) | 20/100 | 0-200/0-2000 | mg |
| Baicalin *Scutellaria baicalensis*/(Baical Skullcap: Extract, Powder, Concentrate) | 20/100 | 0-200/0-2000 | mg |
| Myricetin/(Green Tea, Black Tea, Fennel, Parsley: Extract, Powder, Concentrate) | " | " | " |
| Gallic Acid/(Green Tea, Mango, Rhubarb, Cranberry Extract: Extract, Powder, Concentrate) | " | " | " |
| Silymarin, Silybin (Milk Thistle: Extract, Powder, Concentrate) | 20/100 | 0-200/0-2000 | mg |
| (DTD (−)) | | | |
| EGCG/(Green Tea, Oolong Tea, Black Tea) | " | " | " |
| Baicalin *Scutellaria baicalensis*/(Baical Skullcap: Extract, Powder, Concentrate) | " | " | " |
| Quercetin ± glucosides/(Black Tea, Green Tea, Lovage Leaves, Evening Primrose, Mayapple, *Matricaria recutita* (chamomile: Extract, Powder, Concentrate), *Trifolium pratense* (red clover: Extract, Powder, Concentrate), *Althaea officinalis* (marshmallow: Extract, Powder, Concentrate), *Hypericum perforatum* (St john's Wort: Extract, Powder, Concentrate): Extract, Powder, Concentrate) | " | " | " |
| (MO (−)) | | | |
| Histidine | 125 | 0-1000 | mg |
| Ascorbic Acid | " | " | " |
| (MAO (−)) | | | |
| EGCG/(Green Tea, Oolong Tea, Black Tea: Extract, Powder, Concentrate) | " | " | " |
| Gromwell Root/Shikonin ± shikonin derivatives | 300 | 0-2000 | Mg |

TABLE 1-continued

Parkinsons Nutraceutical Formulation/Options for Constituent by
Mechanism & Constituent by Plant Source Serving Size 1
Amount Per Serving

| Formula Constituent | Target | Opt Range | Unit |
|---|---|---|---|
| (6-OHDA (−)) | | | |
| Cytochrome C | 125 | 0-1500 | Mg |
| Pyruvic Acid, Oxaloacetate or a-ketoglutarate | 1000 | 0-10000 | Mg |
| N-Acetyl-L-Cysteine | " | " | " |
| L-Glutathione | " | " | " |
| Zingerone/(Ginger: Extract, Powder, Concentrate) | 20/100 | 0-200/0-2000 | Mg |
| ($H_2O_2$ (−)) | | | |
| Morin/(White Bulberry: Extract, Powder, Concentrate) | " | " | " |
| L-Glutathione | " | " | " |
| Vitamin A (ie. Beta-Carotene; Retinyl Acetate) | " | " | " |
| Sodium Pyruvate | " | " | " |
| N-Acetyl-L-Cysteine | " | " | " |
| EGCG/(Green Tea, Oolong Tea, Black Tea: Extract, Powder, Concentrate) | " | " | " |
| Caffeic Acid/(Sweet Basil, Thyme, Pear, *Propolis*, Celery seed, *Echinacea*: Extract, Powder, Concentrate) | " | " | " |
| Ferulic Acid/(Pineapple, Dill, Orange, Grapefruit, Lemon, *Angelica sinensis* (dong quai: Extract, Powder, Concentrate), *Melissa officinalis* (lemon balm: Extract, Powder, Concentrate) | " | " | " |
| Quercetin ± glucosides/(Black Tea, Green Tea, Lovage Leaves, Evening Primrose, Mayapple, *Matricaria recutita* (chamomile: Extract, Powder, Concentrate), *Trifolium pratense* (red clover: Extract, Powder, Concentrate), *Althaea officinalis* (marshmallow: Extract, Powder, Concentrate), *Hypericum perforatum* (St john's Wort: Extract, Powder, Concentrate): Extract, Powder, Concentrate) | " | " | " |
| Vanillic Acid/(*Althaea officinalis*-Marshmallow: Extract, Powder, Concentrate) | " | " | " |
| Pycnogenol/(*Pinus Maritima*, Canadian Spruce, Grape Seeds: Extract, Powder, Concentrate) | " | " | " |
| Pyrogallol | 10 | 0-100 | Mg |
| Gallic Acid/(Green Tea, Mango, Rhubarb, Cranberry Extract: Extract, Powder, Concentrate) | " | " | " |
| Chlorogenic acid (Coffee, Sunflower seeds, Blueberry, Bilbeny: Extract, Powder, Concentrate) | " | " | " |
| Resveratrol/(Grapes, Mulberries: Extract, Powder, Concentrate) | " | " | " |
| Acacetin/(*Propolis*, *Gingko Biloba*: Extract, Powder, Concentrate) | " | " | " |
| Fisetin/(*acacia*: Extract, Powder, Concentrate) | " | " | " |
| Isorhamnetin/(Parsely, Dill, *Calendula officinalis* (calendula: Extract, Powder, Concentrate), *Matricaria recutita* (chamomile: Extract, Powder, Concentrate), *Trifolium pratense* (red clover: Extract, Powder, Concentrate): Extract, Powder, Concentrate) | " | " | " |
| Robinetin | 0 | 0-500 | Mg |
| Myricetin/(Green Tea, Black Tea, Fennel, Parsley: Extract, Powder, Concentrate) | " | " | " |
| Hyperoside/*Filipendula ulmaria* (Meadowsweet: Extract, Powder, Concentrate) | 20/100 | 0-200/0-2000 | mg |
| Sesamol/Sesame Seeds, Sesame Oil | 20/100 | 0-200/0-2000 | mg |
| (GSH-PX (+)) | | | |
| L-Glutathione | " | " | " |
| Selenium | 200 | 0-500 | μg |
| Vitamin E (alpha Tocopheryl Acetate) | " | " | " |
| NADPH | 10 | 0-250 | mg |
| Tumeric (Curcumin) | 20/100 | 0-200/0-2000 | mg |
| (SOD (+)) | | | |
| L-Methionine | 200 | 0-750 | mg |
| Manganese (ie. aminoate) | 5 | 0-10 | mg |
| Zinc (ie. amino acid chelate) | 30 | 0-100 | mg |
| *Propolis* (Bee Pollen) | 50 | 0-500 | mg |
| (AD (+)) | | | |
| L-Glutathione | " | " | " |
| NAD+ | 10 | 0-250 | mg |
| (PNMT (−)) | | | |
| Magnesium Oxide | " | " | " |
| Caffeine | 10 | 0-100 | mg |

TABLE 1-continued

Parkinsons Nutraceutical Formulation/Options for Constituent by Mechanism & Constituent by Plant Source Serving Size 1
Amount Per Serving

| Formula Constituent | Target | Opt Range | Unit |
|---|---|---|---|
| (NNMT (−)) | | | |
| Magnesium (ie. oxide) | " | " | " |
| Xanthosine/caffeine precursors (green tea) | 25/100 | 0-500/0-2000 | mg |
| Berberine/(phellodendron, coptis, jateorrhizine, coptisine, palmatine and columbamine, barberry, goldenseal, and Oregon grape) | 10/100 | 0-200/0-2000 | mg |
| (FE-C (−)) | | | |
| Morin/(White Bulberry: Extract, Powder, Concentrate) | " | " | " |
| Sesamol/Sesame Seeds, Sesame Oil | " | " | " |
| Myrrh | 100 | 0-2000 | mg |
| Ferulic Acid/(Pineapple, Dill, Orange, Grapefruit, Lemon, *Angelica sinensis* (dong quai: Extract, Powder, Concentrate), *Melissa officinalis* (lemon balm: Extract, Powder, Concentrate) | " | " | " |
| Corriandor, clove, cinnamon | 100 | 0-2000 | mg |
| Rosemary, Sage, Oregano Extract, Powder, Concentrate | 100 | 0-2000 | mg |
| Caffeic Acid/(Sweet Basil, Thyme, Pear, *Propolis*, Celery seed, *Echinacea*: Extract, Powder, Concentrate) | " | " | " |
| Ferulic Acid/(Pineapple, Dill, Orange, Grapefruit, Lemon, *Angelica sinensis* (dong quai: Extract, Powder, Concentrate), *Melissa officinalis* (lemon balm: Extract, Powder, Concentrate) | " | " | " |
| EGCG/(Green Tea, Oolong Tea, Black Tea: Extract, Powder, Concentrate) | " | " | " |
| Phytic Acid/(Pumpkin Seed, Wheat Seed: Extract, Powder, Concentrate) | " | " | " |
| Quercetin ± glucosides/(Black Tea, Green Tea, Lovage Leaves, Evening Primrose, Mayapple, *Matricaria recutita* (chamomile: Extract, Powder, Concentrate), *Trifolium pratense* (red clover: Extract, Powder, Concentrate), *Althaea officinalis* (marshmallow: Extract, Powder, Concentrate), *Hypericum perforatum* (St john's Wort: Extract, Powder, Concentrate): Extract, Powder, Concentrate) | " | " | " |
| Rutin/(Apricot, Parsely, Buckwheat, Orange, Chamomile, Meadowsweet: Extract, Powder, Concentrate) | " | " | " |
| Luteolin/(Thyme, Parsely, Peppermint, Celery Seed, Chamomile, Rosemary, Fenugreek and *Ginko Biloba*: Extract, Powder, Concentrate) | " | " | " |
| Myricetin/(Green Tea, Black Tea, Fennel, Parsley: Extract, Powder, Concentrate) | " | " | " |
| (Synuclein Aggregation (−)) | | | |
| Magnesium | " | " | " |
| Methionine | " | " | " |
| Ascorbic Acid | " | " | " |
| L-Glutathione | " | " | " |
| N-Acetyl-L-Cysteine | " | " | " |
| EGCG/(Green Tea, Oolong Tea, Black Tea: Extract, Powder, Concentrate) | " | " | " |
| L-Cysteine | | | |
| (HO-1 (−)) | | | |
| L-Cysteine | " | " | " |
| Ascorbic Acid | " | " | " |
| Resevatrol/(Grapes: Extract, Powder, Concentrate) | " | " | " |
| L-Glutathione | " | " | " |
| N-Acetyl-L-Cysteine | " | " | " |
| Quercetin ± glucosides/(Black Tea, Green Tea, Lovage Leaves, Evening Primrose, Mayapple, *Matricaria recutita* (chamomile: Extract, Powder, Concentrate), *Trifolium pratense* (red clover: Extract, Powder, Concentrate), *Althaea officinalis* (marshmallow: Extract, Powder, Concentrate), *Hypericum perforatum* (St john's Wort: Extract, Powder, Concentrate): Extract, Powder, Concentrate) | " | " | " |
| Apigenin/(Dried Parsely, Chamomile, Celery Seed: Extract, Powder, Concentrate) | " | " | " |
| Kaempferol/(Black Tea, Green Tea, Capers, Dill: Extract, Powder, Concentrate) | " | " | " |
| (GLUergic (−)/GABAergic (+)) | | | |
| Zinc Salts | " | " | " |
| Histidine | " | " | " |
| Magnesium (ie. Magnesium Oxide) | " | " | " |
| L-Taurine | 75 | 0-500 | mg |
| Potassium | 100 | 0-500 | mg |
| L-Glycine | 75 | 0-500 | mg |

TABLE 1-continued

Parkinsons Nutraceutical Formulation/Options for Constituent by Mechanism & Constituent by Plant Source Serving Size 1
Amount Per Serving

| Formula Constituent | Target | Opt Range | Unit |
|---|---|---|---|
| (MAPK/NF-KAPPA-B/iNOS/COX-2 (−)) | | | |
| Butein/(*Rhus verniciflua* Stokes, *Faba* beans: Extract, Powder, Conc) | " | " | " |
| Chrysin/(Carrot, Sour Cherry, Skullcap: Extract, Powder, Concentrate) | " | " | " |
| Quercetin ± glucosides/(Black Tea, Green Tea, Lovage Leaves, Evening Primrose, Mayapple, *Matricaria recutita* (chamomile), *Trifolium pratense* (red clover), *Althaea officinalis* (marshmallow), *Hypericum perforatum* (St john's Wort): Extract, Powder, Concentrate) | " | " | " |
| Apigenin/(Dried Parsely, Chamomile, Celery Seed: Extract, Powder, Concentrate) | " | " | " |
| Hydroxychalcones | 10 | 0-250 | mg |
| Diosmetin/(Rosemary, Marshmallow: Extract, Powder, Concentrate) | 20/100 | 0-200/0-2000 | mg |
| Luteolin/(Thyme, Parsely, Peppermint, Celery Seed, Chamomile, Rosemary, Fenugreek and *Ginko Biloba*: Extract, Powder, Concentrate) | " | " | " |
| EGCG/(Green Tea, Oolong Tea, Black Tea: Extract, Powder, Concentrate) | " | " | " |
| Scutellarein/(Skullcap: Extract, Powder, Concentrate) | " | " | " |
| Anthocyanins/Proanthocyanidin/(Açai, blackcurrant, chokeberry, orange, blackberry, black raspbeny, raspberry, wild blueberry, cheny, red currant, red grape, red wine, seed coat of black soybean (*Glycine max* L. Merr.), black chokeberry, bilberry, *cacao* beans, *sorghum* and cinnamon.: Extract, Powder, Concentrate) | " | " | " |
| Biopterin | 25 | 0-200 | µg |
| Silymarin, Silybin (Milk Thistle: Extract, Powder, Concentrate) | 20/100 | 0-200/0-2000 | mg |
| Zinc | " | " | " |
| Selenium | " | " | " |
| (PDE (−)) | | | |
| Butein/(*Rhus verniciflua* Stokes, *Faba* beans: Extract, Powder, Conc) | " | " | " |
| Cirsimarin | 20 | 0-50 | mg |
| Anthocyanins/Proanthocyanidin/(Açai, blackcurrant, chokeberry, orange, blackberry, black raspberry, raspberry, wild blueberry, cherry, red currant, red grape, red wine, seed coat of black soybean (*Glycine max* L. Merr.), black chokeberry, bilberry, *cacao* beans, *sorghum* and cinnamon.: Extract, Powder, Concentrate) | " | " | " |
| Grape Seed Extract | 100 | 0-2000 | mg |
| Diosmetin/(Rosemary, Marshmallow: Extract, Powder, Concentrate) | " | " | " |
| Luteolin/(Thyme, Parsely, Peppermint, Celery Seed, Chamomile, Rosemary, Fenugreek and *Ginko Biloba*: Extract, Powder, Concentrate) | " | " | " |
| Quercetin ± glucosides/(Black Tea, Green Tea, Lovage Leaves, Evening Primrose, Mayapple, *Matricaria recutita* (chamomile), *Trifolium pratense* (red clover), *Althaea officinalis* (marshmallow), *Hypericum perforatum* (St john's Wort): Extract, Powder, Concentrate) | " | " | " |
| Apigenin/(Dried Parsely, Chamomile, Celery Seed: Extract, Powder, Concentrate) | " | " | " |
| Caffeic Acid/(Sweet Basil, Thyme, Pear, *Propolis*, Celery seed, *Echinacea*: Extract, Powder, Concentrate) | " | " | " |
| Catechin/(Green Tea, Oolong Tea, Black Tea: Extract, Powder, Concentrate) | 20/100 | 0-200/0-2000 | mg |
| Amentoflavone/(*Ginkgo biloba*: Extract, Powder, Concentrate) | " | " | " |
| Theophylline/(Tea) | 10/100 | 0-100/0-2000 | mg |
| Scutellarein/(Skullcap: Extract, Powder, Concentrate) | " | " | " |
| Phloretin/(Rosaceae Apple: Extract, Powder, Concentrate) | " | " | " |
| Daidzein, Biochanin A/(Red Clover, Soy, *Alfalfa*: Extract, Powder, Concentrate) | 20/100 | 0-200/0-2000 | mg |
| Malvidin (Grapes, Bilberry, Raspberries, Blueberry: Extract, Powder, Concentrate) | 20/100 | 0-200/0-2000 | mg |

TABLE 2

Sample Parkinson's Nutraceutical - Preferred Formulation Components: Serving Size 1

| Amount Per Serving Component | Target | Range | Unit |
|---|---|---|---|
| Amino Acid Selection | | | |
| L-Glycine (r) | 75 | 0-500 | mg |
| L-Histidine (r) | 125 | 0-1000 | mg |
| L-Cysteine or NAC (r) | 500 | 0-2000 | mg |
| L-Glutathione (r) | 250 | 0-2000 | mg |
| L-Methionine (r) | 200 | 0-750 | mg |
| L-Serine (r) | 100 | 0-400 | mg |
| L-Taurine (r) | 75 | 0-500 | mg |
| Acetyl-L-Carnitine (r) | 150 | 0-3000 | mg |
| L-Lysine (r) | 150 | 0-2000 | mg |
| Chemical or Micro-Macronutrients | | | |
| Alpha-Lipoic Acid (r) | 100 | 0-2000 | mg |
| Ascorbic Acid (r) | 50 | 0-250 | mg |
| Betaine (ie. Hydrochloride) (r) | 75 | 0-350 | mg |
| Biopterin (o) | 25 | 0-200 | μg |
| Biotin (r) | 300 | 0-1200 | μg |
| Caffeine/Theophylline (o) | 10 | 0-100 | mg |
| Coenzyme Q10 (r) | 35 | 0-1000 | mg |
| Creatine (ie. Pyruvate) (r) | 200 | 0-3000 | mg |
| Cytochrome C (o) | — | 0-1500 | mg |
| Folic Acid (r) | 800 | 0-3000 | μg |
| Fructose or Fruc 1,6, BP (r) | 400 | 0-3000 | mg |
| Malic Acid (o) | 25 | 0-3000 | mg |
| OAA/Succinate (ie. sodium) (r) | 500 | 0-10000 | mg |
| Pantothenic Acid (r) | 100 | 0-400 | mg |
| Pyrodoxine (Vitamin B-6) (r) | 400 | 0-2000 | mg |
| Pyruvic acid (ie. Sodium) (r) | 1500 | 0-10000 | mg |
| Riboflavin (Vitamin B-2)(r/o) | 25 | 0-300 | mg |
| Thiamin (ie. Hydrochloride) (r) | 100 | 0-400 | mg |
| Vit A (Carotene; Ret Acetate) (r) | 5000 | 0-15000 | IU |
| Vit B12 (Cyanocobalamin) (r) | 100 | 0-350 | μg |
| Vit B-3 (Nicotinamide) (r) | 250 | 0-1000 | mg |
| Vit D (ie. Cholecalciferol) (r) | 400 | 0-600 | IU |
| Vit E (ie. Tocopheryl Ace.) (r) | 300 | 0-600 | IU |
| Vit K (Phytonadione) (r) | 80 | 0-120 | mcg |
| Element Selection | | | |
| Phosphorous (r) | 50 | 0-300 | mg |
| Potassium (r) | 100 | 0-500 | mg |
| Magnesium (ie. Oxide) (r) | 300 | 0-1000 | mg |
| Manganese (ie. Aminoate) (o) | 5 | 0-10 | mg |
| Selenium (ie. Sodium) (r) | 200 | 0-500 | μg |
| Zinc (ie. Amino acid chelate) (r) | 30 | 0-100 | mg |
| Chromium (ie. Picolinate) (r) | 75 | 0-250 | μg |
| Plants - Selected by Chemical Composition - Table 1 | | | |
| *Aloe Vera* (200:1) (r) (plants, extracts, powders, concentrates) | 20 | 0-400 | mg |
| Addition Plant Options | 100 | 0-2000 | Mg |
| Apple (r)/Acai (r) | Hyssop (o) | | |
| Apricot (r) | Licorice (o) | | |
| Barberry (o) | Marshmallow (o) | | |
| Bilberry (r) | Meadowsweet (o) | | |
| Blueberry (r) | Milk Thistle (o) | | |
| Basil (o) | Mulberry (r) | | |
| Calendula (o) | Myrrh (o) | | |
| Carrot (r) | Orange/Lemon (r) | | |
| Celery Seed (o) | Oregano (o) | | |
| Chamomile (o) | Parsley (o) | | |
| Cilantro (o) | Pear (r) | | |
| Cinnamon/Clove (o) | Peppermint (o) | | |
| Chokeberry (r) | Proprolis (o) | | |
| Cranberry (r) | Pumpkin Seed (o) | | |
| Dill (o) | Raspberries (r) | | |
| *Echinacea* (o) | Rosemary (o) | | |
| Elderberry (r) | Sage (o) | | |
| Faba Bean (o) | Strawberry (r) | | |
| Fennel (o) Garlic (o) | Skull cap (o) | | |
| *Ginko Biloba* (o) | Sour/Sweet Cherry (r) | | |
| Grape Seed/Skin (r) | Sorghum (o) | | |
| Grapefruit (o) | Soybean B seed coat (r) | | |
| Green Tea (r) | Tumeric (o) | | |
| Gromwell Root ® | Thyme (o) | | |
| Opt. Polyphenolic Compounds (0-200 mg) | | | |
| Acacetin, Apigenin, Amentoflavone, Anthocyanins, Berberine, Baicalein, Butein, Caffeic Acid, Chrysin, Cinnamic Acid, Curcumin, Coumarin, Cyanidin, Delphinidin, Diosmin, EGCG, Ellagic acid, Esculetin, Ferulic Acid, Fisetin, Gallic Acid, Ginkgetin, Hypolatein, Isoginkgetin, Isoliquiritin, Isorhamnetin, Kaempferol, Kenusanone, Kuraridin, Kurarinone, Licuraside, Luteolin, Morin, Malvidin, Myricetin, Naringen, Phloretin, Phytic Acid, Psoralidin, Pycnogenol, Pyrogallol, Quercetin, Resorcinol, Sesamol, Resveratrol, Rutin, Sanggenon D, Scutellarian, Silymarin, Sideritloflavone, Shikonin, Sophorcarpidine, Tetrahydrochalcones, Thymoquinon, Vaicalein, Vanillic Acid, Wogonin, Xanthosine, Zingerone. | | | |
| Oil Selection | | | |
| Canola Oil (o) | 300 | 0-1500 | Mg |
| Evening Primrose Oil (r) | 250 | 0-1500 | Mg |
| Fish Oil (r) | 300 | 0-1500 | Mg |
| Sesame Oil (r) | 50 | 0-1500 | Mg |

(r) = Recommended,
(o) = Optional

The invention as described in this embodiment claims the formulation and use thereof. Of important note, recent studies in our lab using mice indicate strong importance of anthocyanins and fruit extracts in preventing the pathological decay of the striatal tract. With this in mind, the primary base will be comprised of a fruit component or polyphenol fraction of a fruit extract supplemented with Anaerobic (+), optionally combined with lysine. The formulation in total can take any form including but not limited to a dietary supplement, food, beverage, and or any other pharmaceutical or nutraceutical preparation—wherein said formulation is for the specific application to Parkinson's Disease to achieve any desired clinical benefit. The formulation may contain the active ingredients as described in the presence or absence of fillers, preservatives, solvents, carriers or the like. If a carrier is present, it may be comprised of solid, liquid, powder, paste, gel, tablet, granule, foam, pack, ointment, aerosol, solvent, tablet, diluent, capsule, pill, drink, liposome, syrup, solution, suppository, emulsion, suspension, dispersion, food, bolus, electuary, paste or other bio-delivery system or agent. An acceptable carrier is also defined as any safe material that acts as a vehicle for delivery including but not limited to: cellulose, silica, water, saline, starches, sugars, flavorings, gels, lipids, waxes, paraffin derivatives, glycerols, solvents, oils, proteins, talc, glycols, electrolyte solutions, alcohols, gums, fillers, binders, cellulose, magnesium stearate, emulsifiers, humectants, preservatives, buffers, colorants, emollients, foaming agents, sweeteners, thickeners, surfactants, additives, solvents, lubricants or the like. Formulations that include pharmaceutically acceptable carriers and delivery systems may be adapted for varying route of administration such as topical, enteral and parenteral including but not limited to: oral, rectal, nasal, subcutaneous, intramuscular, intravenous, intraperitoneal, transmucosal, transdermal, epicutaneous, intracutaneous or other suitable route. Formulations adapted for oral administration may contain a predetermined quantity of the active ingredient and take the form of sprays, liquids, syrups, beverages, capsules, powders, granules, solutions, suspensions, tablets, food, lozenges or any other form in which the active ingredients are taken by mouth and absorbed through the alimentary canal.

The incorporation of plant compounds in the formulation may include part or whole plant including but not limited to the root, seed, nut, stalk, bark, vegetable, fruit, hull, bud, leaf, flower, bulb or entire plant. Plant constitutents can take the form of solids, liquid, concentrates, extracts or any other. If prepared by extract, whole plants can be prepared by drying procedures, where the fresh herbs are dried at very low temperature, macerated into an extract which is comprised of one or more of the following: grain alcohol, distilled water, glycerine or vinegar. These can also include any liquid, chemical, alcohol, lipophilic oil based solvents or acetone. Depending upon the strength of the herbal extract, dry herb menstrumm ratios can vary (w/v) are a typically between 1:5-4:5. Typically herbal extracts can be stored in a sterile closed container (glass or suitable), in a warm dry area, away from light for about 0.5-2 weeks with intermittent stirring. The extract can then filtered to remove particulates and stored at a cool temperature in an amber container to prevent exposure to light.

The formulation of substances that comprise this invention are not necessarily limited to definition by mechanism, since these agents may also meditate effects through other various means. On the other hand, the invention discloses a means through a mechanism to treat or prevent PD, by specifically and intentionally creating a formulation that combines one or more compounds classified under formula components A, B and C and corresponding subsections as defined above. The invention includes any or all type of modifications or methods to the development of a formula to achieve these means that are obvious to one skilled in the art, but not described in the aforementioned and adhere to the scope of the invention. Although it is designed to ameliorate PD, the treatment may also be useful as a nutraceutical for Alzheimer's Disease, stroke, any other central nervous system or peripheral degenerative disease or diseases related to energy failure or dopaminergic cell death in which clinical benefit is achieved.

What is claimed is:

1. A composition useful for the treatment of Parkinson's disease comprising a therapeutically effective amount of a composition comprising:
   alpha-ketoglutarate;
   succinic acid;
   pyruvate;
   vitamin B6;
   lysine;
   biochanin A, wherein said biochanin A is optionally derived from alfalfa, soybeans, or red clover;
   diosmin, wherein said diosmin is optionally derived from hyssop or rosemary;
   butein, wherein said butein is optionally derived from *Rhus verniciflua* or faba bean;
   naringin, wherein said naringin is optionally derived from orange;
   strawberry component selected from strawberry powder, strawberry extract, strawberry concentrate, or strawberry juice;
   bilberry component selected from bilberry powder, bilberry extract, bilberry concentrate, or bilberry juice;
   chromium;
   zinc;
   Vitamin B3;
   Magnesium;
   NADH;
   quercetin, wherein said quercetin is optionally derived from Marshmallow or St. John's Wort; and
   a pharmaceutically acceptable carrier.

2. The composition of claim 1 further comprising one or more ingredient selected from the group consisting of luteolin, apigenin, ascorbate, N-acetyl-L-cysteine, glutathione, beta-carotene, L-carnitine, riboflavin, coenzyme Q10, thiamin, lipoic acid, pantothenic acid, biotin, creatine, phosphorus, acacetin, *Scutellaria baicalensis*, caffeic acid, chlorogenic acid, robinetin, fisetin, gallic acid, hyperoside, *Filipendula ulmaria*, isorhamnetin, pycnogenol, pyrogallol, mulberry, vanillic acid, kaempferol, clove, cinnamon, myrrh, ferulic acid, cysteine, methionine, morin, phytic acid, quercetin glucosides, sage, oregano, rutin, silymarin, silybin, sesamol, aurantinidin, cyanidin, delphinidin, europinidin, luteolinidin, pelargonidin, malvidin, peonidin, petunidin, rosinidin, rosmarinic acid, cinnamic acid, omega 3 fatty acid, gromwell root, aloin, sanggenon, scutellarein, sophoraflavone G, sophorcarpidine, tetrahydroxychalcone, wogonin, chrysin, coumarin, cystamine, daphnetin, esculetin, fraxetin, galangin, isoliquiritin, licuraside, licochalcone, ginkgetin, ginkolide, histidine, hydroxychalcone, methylchalcone, hypolatein, isoginkgetin, kenusanone A, kuraridin, kurarinone, ochnaflavone, psoralidin, resorcinol, manganese, selenium, tocopherol, turmeric, amentoflavone, biopterin, cirsimarin, daidzein, phloretin, caffeine, xanthosine, berberine, cytochrome C, histidine, taurine, potassium, glycine, vitamin B12, folic acid, serine, betaine, vitamin A, vitamin D, vitamin E, vitamin K, thymoquinone, EGCG, resveratrol, apple, pear, blueberry, grape seed extract, cherry, elderberry, chokeberry, carrot, cranberry, apricot, acai, and raspberry.

3. The composition of claim 1 wherein said pharmaceutically acceptable carrier is selected from the group consisting of cellulose, silica, water, saline, starches, sugars, flavorings, gels, lipids, waxes, paraffin, glycerols, oils, proteins, talc, glycols, electrolyte solutions, alcohols, gums, fillers, binders, cellulose, magnesium stearate, emulsifiers, humectants, preservatives, buffers, colorants, emollients, foaming agents, sweeteners, thickeners, surfactants, additives, solvents, lubricants, and combinations thereof.

4. The composition of claim 1 wherein said composition is in a form selected from the group consisting of food, drink, solid, liquid, powder, paste, gel, tablet, granule, foam, pack, ointment, aerosol, solvent, tablet, diluent, capsule, pill, liposome, syrup, solution, suppository, emulsion, suspension, dispersion, bolus, electuary, and paste.

* * * * *

UNITED STATES PATENT AND TRADEMARK OFFICE
CERTIFICATE OF CORRECTION

| | | |
|---|---|---|
| PATENT NO. | : 8,367,121 B2 | Page 1 of 1 |
| APPLICATION NO. | : 12/658307 | |
| DATED | : February 5, 2013 | |
| INVENTOR(S) | : Mazzio et al. | |

It is certified that error appears in the above-identified patent and that said Letters Patent is hereby corrected as shown below:

In the Specification

Column 1, line 19, please amend as follows:

This invention was made with government support under RCMI G12 RR 03020 which was awarded by the National Institutes of Health. The government has certain rights in the invention.

Signed and Sealed this
Twenty-seventh Day of October, 2015

Michelle K. Lee
*Director of the United States Patent and Trademark Office*